United States Patent
Bryant et al.

(10) Patent No.: US 10,758,284 B2
(45) Date of Patent: Sep. 1, 2020

(54) WASHER ASSEMBLY FOR STABILIZING A BONE

(71) Applicant: Cable Fix LLC, Hernando, MS (US)

(72) Inventors: Carey Bryant, Hernando, MS (US); William Ricci, Richmond Heights, MO (US); Mark Brinker, Houston, TX (US)

(73) Assignee: CABLE FIX LLC, Hernando, MS (US)

( * ) Notice: Subject to any disclaimer, the term of this patent is extended or adjusted under 35 U.S.C. 154(b) by 579 days.

(21) Appl. No.: 15/399,063

(22) Filed: Jan. 5, 2017

(65) Prior Publication Data

US 2017/0156775 A1 Jun. 8, 2017

Related U.S. Application Data

(63) Continuation-in-part of application No. 14/961,499, filed on Dec. 7, 2015.

(51) Int. Cl.
| | |
|---|---|
| *A61B 17/86* | (2006.01) |
| *A61B 17/84* | (2006.01) |
| *A61B 17/82* | (2006.01) |
| *A61B 17/68* | (2006.01) |
| *A61B 17/56* | (2006.01) |

(52) U.S. Cl.
CPC ........ *A61B 17/8685* (2013.01); *A61B 17/683* (2013.01); *A61B 17/82* (2013.01); *A61B 17/84* (2013.01); *A61B 17/86* (2013.01); *A61B 17/842* (2013.01); *A61B 2017/564* (2013.01); *A61B 2017/681* (2013.01)

(58) Field of Classification Search
CPC ...... A61B 17/82; A61B 17/683; A61B 17/842
See application file for complete search history.

(56) References Cited

U.S. PATENT DOCUMENTS

| | | | |
|---|---|---|---|
| 479,938 A | 8/1892 | Fredlihp | |
| 899,612 A | 9/1908 | Phillips | |
| 2,489,870 A * | 11/1949 | Dzus | A61B 17/683 411/339 |
| 3,166,072 A | 1/1965 | Sullivan, Jr. | |
| 4,060,089 A | 11/1977 | Noiles | |
| 4,532,927 A | 8/1985 | Miksza, Jr. | |
| 4,534,350 A | 8/1985 | Golden et al. | |
| 4,534,352 A | 8/1985 | Korthoff | |
| 4,548,202 A | 10/1985 | Duncan | |
| 4,573,469 A | 3/1986 | Golden et al. | |

(Continued)

*Primary Examiner* — David W Bates
(74) *Attorney, Agent, or Firm* — Kunzler Bean & Adamson

(57) ABSTRACT

Disclosed herein is a washer assembly for use with a bone. The washer assembly comprises a first portion, comprising a first washer, a first stem non-movably fixed to and extending from the first washer, and a first internal channel defined by the first washer and the first stem. The washer additionally includes a second portion, comprising a second washer, a second stem non-movably fixed to and extending from the second washer, and a second internal channel defined by the second washer and the second stem. The first portion is movable relative to the second portion, to adjust a distance between the first washer and the second washer, and the first internal channel of the first washer is retained in coaxial alignment with the second internal channel of the second washer as the first portion moves relative to the second portion.

20 Claims, 16 Drawing Sheets

(56) References Cited

U.S. PATENT DOCUMENTS

| | | | |
|---|---|---|---|
| 4,610,250 A | 9/1986 | Green | |
| 4,754,758 A | 7/1988 | Lehmann | |
| 4,932,960 A | 6/1990 | Green | |
| 5,358,510 A | 10/1994 | Luscombe et al. | |
| 5,478,353 A | 12/1995 | Yoon | |
| 5,620,452 A | 4/1997 | Yoon | |
| 5,665,109 A | 9/1997 | Yoon | |
| 5,797,932 A | 8/1998 | Min et al. | |
| 5,919,194 A * | 7/1999 | Anderson | A61B 17/683 606/313 |
| 5,984,001 A | 11/1999 | Larsen et al. | |
| 6,276,032 B1 | 8/2001 | Nortman et al. | |
| 6,302,887 B1 * | 10/2001 | Spranza | A61B 17/683 411/338 |
| 6,712,830 B2 | 3/2004 | Esplin | |
| 6,966,919 B2 | 11/2005 | Sixto et al. | |
| 7,033,378 B2 | 4/2006 | Smith et al. | |
| 7,094,251 B2 | 8/2006 | Bonutti et al. | |
| 7,678,122 B2 | 3/2010 | Kortenbach et al. | |
| 7,854,750 B2 | 12/2010 | Bonutti et al. | |
| 7,985,241 B2 | 7/2011 | Smith et al. | |
| 8,080,020 B2 | 12/2011 | Kortenbach et al. | |
| 8,114,100 B2 | 2/2012 | Smith et al. | |
| 8,162,977 B2 | 4/2012 | Bonutti et al. | |
| 8,454,628 B2 | 6/2013 | Smith et al. | |
| 8,613,750 B2 | 12/2013 | Smith et al. | |
| 8,728,133 B2 * | 5/2014 | Fell | A61B 17/8076 606/320 |
| 9,039,596 B2 | 5/2015 | Sater | |
| 9,220,503 B2 | 12/2015 | Ranchod | |
| 9,247,963 B2 * | 2/2016 | Kollmer | A61B 17/683 |
| 9,265,543 B2 * | 2/2016 | Gephart | A61B 17/8076 |
| 9,387,019 B2 * | 7/2016 | Duggal | A61B 17/683 |
| 9,788,827 B2 | 10/2017 | Miksza et al. | |
| 9,907,597 B2 * | 3/2018 | Kollmer | A61B 17/8866 |
| 10,179,016 B1 * | 1/2019 | Bryant | A61B 17/8861 |
| 2001/0051815 A1 | 12/2001 | Esplin | |
| 2002/0029044 A1 | 3/2002 | Monassevitch et al. | |
| 2002/0091391 A1 * | 7/2002 | Cole | A61B 17/0401 606/916 |
| 2004/0044366 A1 | 3/2004 | Bonutti et al. | |
| 2004/0059349 A1 | 3/2004 | Sixto et al. | |
| 2004/0059354 A1 | 3/2004 | Smith et al. | |
| 2004/0059358 A1 | 3/2004 | Kortenbach et al. | |
| 2007/0032825 A1 | 2/2007 | Bonutti et al. | |
| 2008/0046007 A1 | 2/2008 | Schwemberger et al. | |
| 2008/0046008 A1 | 2/2008 | Smith et al. | |
| 2008/0097430 A1 | 4/2008 | Berstein et al. | |
| 2008/0108897 A1 | 5/2008 | Bonutti et al. | |
| 2008/0140095 A1 | 6/2008 | Smith et al. | |
| 2008/0147116 A1 | 6/2008 | Smith et al. | |
| 2008/0149685 A1 | 6/2008 | Smith et al. | |
| 2009/0171357 A1 * | 7/2009 | Justin | A61B 17/82 606/60 |
| 2010/0179568 A1 | 7/2010 | Kortenbach et al. | |
| 2010/0198258 A1 | 8/2010 | Heaven et al. | |
| 2010/0331892 A1 * | 12/2010 | Fell | A61B 17/8076 606/286 |
| 2011/0040307 A1 | 2/2011 | Ranchod | |
| 2011/0092993 A1 | 4/2011 | Jacobs | |
| 2011/0137356 A1 * | 6/2011 | Kollmer | A61B 17/683 606/324 |
| 2011/0201877 A1 | 8/2011 | Sater | |
| 2012/0065638 A1 | 3/2012 | Moore | |
| 2012/0130374 A1 | 5/2012 | Bouduban et al. | |
| 2012/0143247 A1 | 6/2012 | Smith et al. | |
| 2014/0364905 A1 | 12/2014 | Lunn et al. | |
| 2016/0038186 A1 * | 2/2016 | Herzog | A61B 17/685 606/304 |
| 2016/0081686 A1 | 3/2016 | Miksza et al. | |
| 2016/0100835 A1 | 4/2016 | Linder et al. | |
| 2016/0346023 A1 | 12/2016 | Bouduban et al. | |
| 2017/0156738 A1 | 6/2017 | Ricci et al. | |
| 2017/0156771 A1 | 6/2017 | Brinker et al. | |
| 2017/0156772 A1 | 6/2017 | Brinker et al. | |
| 2017/0156774 A1 | 6/2017 | Bryant et al. | |
| 2017/0156779 A1 | 6/2017 | Bryant et al. | |
| 2017/0156847 A1 | 6/2017 | Ricci et al. | |
| 2018/0055550 A1 | 3/2018 | Bryant et al. | |
| 2019/0083155 A1 * | 3/2019 | Bryant | A61B 17/683 |

* cited by examiner

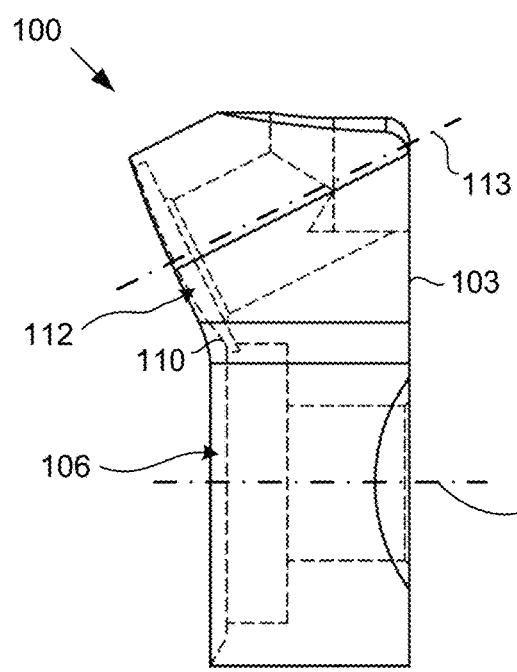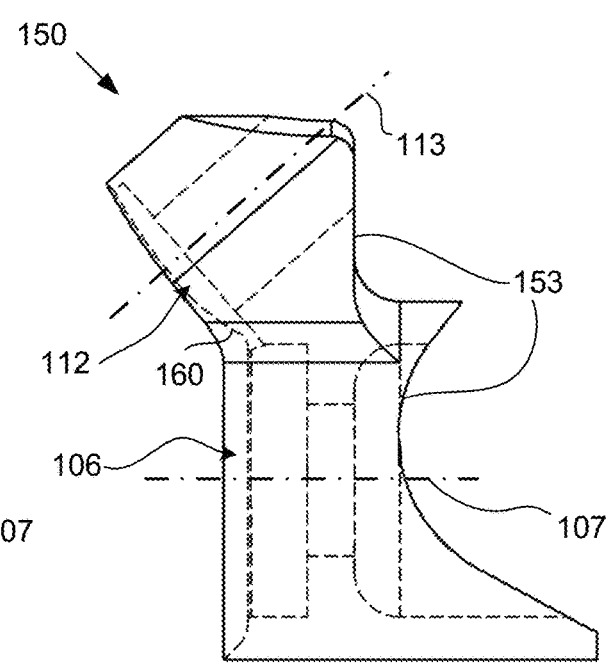
Fig. 1C
Fig. 1D

WASHER ASSEMBLY FOR STABILIZING A BONE

CROSS-REFERENCE TO RELATED APPLICATION

This patent application is a continuation-in-part of U.S. patent application Ser. No. 14/961,499, filed Dec. 7, 2015, the entirety of which is incorporated herein by reference.

FIELD

The subject matter of the present disclosure relates generally to washers for supporting a cable relative to bone. More specifically, the present disclosure relates to using a cable washer to support a cable extending from a pass-through hole in a bone or from around a bone.

BACKGROUND

Various medical procedures utilize cables or conventional sutures to secure damaged skeletal tissue or soft tissue. Tissues, such as bones or soft-tissues, that have been fragmented, fractured, broken, torn, pulled, stretched, or otherwise damaged need to be set and held in specific orientations in order to properly heal. Cables or conventional sutures may be useful for stabilizing or connecting torn tissue back together or for facilitating holding bone fragments in place. For example, cerclage cables or conventional sutures can be wrapped around or lie adjacent to bone for fracture reduction, fracture fixation, and crack propagation prevention. However, conventional tools and procedures for utilizing cables or conventional sutures in medical surgeries are generally time-consuming, complex, and usually involve multiple in-situ steps that are difficult to perform.

SUMMARY

From the foregoing discussion, it should be apparent that a need exists for an apparatus, system, and method for fracture reduction, fracture fixation, and crack propagation prevention that overcome the limitations of conventional medical tools and procedures. Beneficially, such an apparatus, system, and method would improve the ease, efficiency, and effectiveness of medical procedures for fracture reduction, fracture fixation, and crack propagation prevention.

The subject matter of the present application has been developed in response to the present state of the art, and in particular, in response to the problems and needs in the art that have not yet been fully solved by currently available medical tools and procedures. For example, the ease, efficiency, and effectiveness of fracture reduction, fracture fixation, and crack propagation prevention is improved by passing the cable through a bone via a drilled hole (or a reamed hole, cut hole, etc.) in the bone and using one or more washers to support the cable. Accordingly, the present disclosure has been developed to provide an apparatus for supporting a through-bone cable extending from a pass-through hole in a bone, and its related systems and methods, that overcome many or all of the above-discussed shortcomings in the art.

Disclosed herein is a washer assembly for supporting at least one cable extending at least one of around a bone or through a pass-through hole formed in the bone. The washer assembly comprises a first portion, comprising a first washer, a first stem non-movably fixed to and extending from the first washer, and a first internal channel defined by the first washer and the first stem. The washer additionally includes a second portion, comprising a second washer, a second stem non-movably fixed to and extending from the second washer, and a second internal channel defined by the second washer and the second stem. The first portion is movable relative to the second portion, to adjust a distance between the first washer and the second washer, and the first internal channel of the first washer is retained in coaxial alignment with the second internal channel of the second washer as the first portion moves relative to the second portion. The preceding subject matter of this paragraph characterizes example 1 of the present disclosure.

The first washer is configured differently than the second washer. The preceding subject matter of this paragraph characterizes example 2 of the present disclosure, wherein example 2 also includes the subject matter according to example 1, above.

The first washer of the first portion comprises a first bone-engaging surface. The second washer of the second portion comprises a second bone-engaging surface. The first bone-engaging surface and the second bone-engaging surface are curved. The preceding subject matter of this paragraph characterizes example 3 of the present disclosure, wherein example 3 also includes the subject matter according to any one of examples 1 and 2, above.

The first bone-engaging surface has a shape different than that of the second bone-engaging surface. The preceding subject matter of this paragraph characterizes example 4 of the present disclosure, wherein example 4 also includes the subject matter according to example 3, above.

The first washer comprises a first external recess contiguous with the first internal channel. The second washer comprises a second external recess contiguous with the second internal channel. The preceding subject matter of this paragraph characterizes example 5 of the present disclosure, wherein example 5 also includes the subject matter according to any one of examples 1 to 4, above.

The second stem of the second portion is nestably inserted within and translationally movable along the first internal channel of the first portion to adjust the distance between the first washer and the second washer. The preceding subject matter of this paragraph characterizes example 6 of the present disclosure, wherein example 6 also includes the subject matter according to any one of examples 1 to 5, above.

An outer diameter of the second stem of the second portion is approximately equal to an inner diameter of the first internal channel of the first portion. The preceding subject matter of this paragraph characterizes example 7 of the present disclosure, wherein example 7 also includes the subject matter according to example 6, above.

The first stem of the first portion is in telescoping engagement with the second stem of the second portion. The preceding subject matter of this paragraph characterizes example 8 of the present disclosure, wherein example 8 also includes the subject matter according to example 6, above.

An inner diameter of the first internal channel of the first portion is larger than an inner diameter of the second internal channel of the second portion. The preceding subject matter of this paragraph characterizes example 9 of the present disclosure, wherein example 9 also includes the subject matter according to example 6, above.

The second stem of the second portion is slidable along the first internal channel of the first portion to adjust a distance between the first washer and the second washer. The preceding subject matter of this paragraph characterizes example 10 of the present disclosure, wherein example 10 also includes the subject matter according to example 6, above.

The first washer comprises a first arm, extending radially away from the first internal channel, and a third internal channel defined by the first arm and spaced apart from the first internal channel. The second washer comprises a second arm, extending radially away from the second internal channel, and a fourth internal channel defined by the second arm and spaced apart from the second internal channel. The preceding subject matter of this paragraph characterizes example 11 of the present disclosure, wherein example 11 also includes the subject matter according to any one of examples 1 to 10, above.

The washer assembly further comprises a fastener threadably engaged with the first internal channel of the first washer and engaged with the second internal channel of the second washer to couple together the first stem of the first washer and the second stem of the second washer, wherein rotation of the fastener relative to the first internal channel of the first washer adjusts the distance between the first washer and the second washer. The preceding subject matter of this paragraph characterizes example 12 of the present disclosure, wherein example 12 also includes the subject matter according to any one of examples 1 to 11, above.

Also disclosed is a washer system, for supporting at least one cable extending at least one of around a bone or through a pass-through hole formed in the bone, that comprises a washer assembly and a coupling element. The washer assembly comprises a first portion, comprising a first washer, a first stem non-movably fixed to and extending from the first washer, and a first internal channel passing through the first washer and the first stem. The washer assembly also comprises a second washer, a second stem non-movably fixed to and extending from the second washer, and a second internal channel passing through the second washer and the second stem. The first portion is movable relative to the second portion, to adjust a distance between the first washer and the second washer, and the first internal channel of the first washer is retained in coaxial alignment with the second internal channel of the second washer as the first portion moves relative to the second portion. The coupling element is releasably coupled to the first portion and the second portion, reversibly decouplable from the first portion and the second portion, and positioned within the first internal channel of the first portion of the washer assembly and within the second internal channel of the second portion of the washer assembly. The coupling element is actuatable to move the first portion relative to the second portion. The preceding subject matter of this paragraph characterizes example 13 of the present disclosure.

The coupling element comprises a first cable. With the first cable positioned within the first internal channel and the second internal channel, a first end portion of the first cable is coupled with the first washer and a second end portion of the first cable is coupled with the second washer. The first cable is tensionable to adjust the distance between the first washer and the second washer. The preceding subject matter of this paragraph characterizes example 14 of the present disclosure, wherein example 14 also includes the subject matter according to example 13, above.

The second stem of the second portion is nestably inserted within and translationally movable along the first internal channel of the first portion to adjust a distance between the first washer and the second washer. The preceding subject matter of this paragraph characterizes example 15 of the present disclosure, wherein example 15 also includes the subject matter according to example 14, above.

An outer diameter of the cable is approximately equal to an inner diameter of second internal channel. The preceding subject matter of this paragraph characterizes example 16 of the present disclosure, wherein example 16 also includes the subject matter according to example 15, above.

The first washer comprises a first external recess contiguous with the first internal channel. The second washer comprises a second external recess contiguous with the second internal channel. The first cable comprises a first stop at one of the first end portion or the second end portion of the first cable, the first stop being seatably engaged with one of the first external recess or the second external recess. The washer system further comprises a first crimp body crimped to the other of the first end portion or the second end portion of the first cable, the first crimp body being seatably engaged with the other of the first external recess or the second external recess. The preceding subject matter of this paragraph characterizes example 17 of the present disclosure, wherein example 17 also includes the subject matter according to any one of examples 15 to 16, above.

The first washer comprises a first arm, extending radially away from the first internal channel, and a third internal channel defined by the first arm and spaced apart from the first internal channel. The second washer comprises a second arm, extending radially away from the second internal channel, and a fourth internal channel defined by the second arm and spaced apart from the second internal channel. The washer system further comprises a second cable comprising a third end portion and a fourth end portion, the third end portion of the second cable being positioned within the third internal channel and coupled with the first arm of the first washer and the fourth end portion of the second cable being positioned within the fourth internal channel and coupled with the second arm of the second washer. The preceding subject matter of this paragraph characterizes example 18 of the present disclosure, wherein example 18 also includes the subject matter according to any one of examples 15 to 17, above.

The first washer comprises a third external recess contiguous with the third internal channel. The second washer comprises a fourth external recess contiguous with the fourth internal channel. The second cable comprises a second stop at one of the third end portion or the fourth end portion of the second cable, the second stop being seatably engaged with one of the third external recess or the fourth external recess. The washer system further comprises a second crimp body crimped to the other of the third end portion or the fourth end portion of the second cable, the second crimp body being seatably engaged with the other of the third external recess or the fourth external recess. The preceding subject matter of this paragraph characterizes example 19 of the present disclosure, wherein example 19 also includes the subject matter according to example 18, above.

The coupling element comprises a fastener threadably engaged with the first internal channel of the first washer and engaged with the second internal channel of the second washer to couple together the first stem of the first washer and the second stem of the second washer. The fastener is rotatable relative to the first internal channel of the first washer to adjust the distance between the first washer and the second washer. The preceding subject matter of this paragraph characterizes example 20 of the present disclosure, wherein example 20 also includes the subject matter according to example 13, above.

A method of reducing and stabilizing at least one of a fracture in, a dislocation of, or a subluxation of at least one bone is also disclosed. The method comprises forming a pass-through hole in at least the one bone and inserting a first stem of a first portion of a washer assembly into the pass-through hole through a first opening of the pass-through hole. The washer assembly further comprises a first washer, to which the first stem is non-movably fixed and from which the first stem extends, and a first internal channel defined by the first washer and the first stem. The method also includes inserting a second stem of a second portion of the washer assembly into the pass-through hole through a second opening of the pass-through hole. The second opening is formed in a first surface of at least the one bone and the first opening being formed in a second surface of at least the one bone. The first surface is opposite the second surface. The washer assembly further comprises a second washer, to which the second stem is non-movably fixed and from which the second stem extends, and a second internal channel defined by the second washer and the second stem. The method further comprises positioning a coupling element within the first internal channel of the first portion and the second internal channel of the second portion. The method also comprises actuating the coupling element to urge the first washer into contact with the first surface of at least the one bone and to urge the second washer into contact with the second surface of at least the one bone. The preceding subject matter of this paragraph characterizes example 21 of the present disclosure.

The coupling element comprises a first cable. The method further comprises nestably inserting the second stem of the second portion into the first internal channel of the first stem of the first portion, passing the first cable through the first internal channel of the first portion and the second internal channel of the second portion, with the first cable positioned within the first internal channel of the first portion and the second internal channel of the second portion, actuating the coupling element comprises tensioning the first cable, and with the first cable tensioned, non-movably fixing a first end portion of the first cable to the first washer and non-movably fixing a second end portion of the first cable to the second washer. The preceding subject matter of this paragraph characterizes example 22 of the present disclosure, wherein example 22 also includes the subject matter according to example 21, above.

The method further comprises self-adjusting a distance between the first washer of the first portion of the washer assembly and the second washer of the second portion of the washer assembly by tensioning the first cable. The preceding subject matter of this paragraph characterizes example 23 of the present disclosure, wherein example 23 also includes the subject matter according to any one of examples 21 to 22, above.

The coupling element comprises a fastener and actuating the coupling element comprises rotating the fastener. The preceding subject matter of this paragraph characterizes example 24 of the present disclosure, wherein example 24 also includes the subject matter according to any one of examples 21 or 23, above.

The method further comprises positioning a second cable about a third surface of at least the one bone between the first surface and the second surface of at least the one bone, passing the second cable through a third internal channel of a first arm of the first washer, and passing the second cable through a fourth internal channel of a second arm of the second washer. The method also comprises, with the second cable positioned within the third internal channel and the fourth internal channel, tensioning the second cable to urge the second cable against the third surface of at least the one bone. The method additionally comprises, with the second cable tensioned, non-movably fixing a third end portion of the second cable to the first arm of the first washer and non-movably fixing a fourth end portion of the second cable to the second arm of the second washer. The preceding subject matter of this paragraph characterizes example 25 of the present disclosure, wherein example 25 also includes the subject matter according to any one of examples 21 to 24, above.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which:

FIG. 1C is a side view of the washer of FIG. 1A, according to one embodiment;

FIG. 1D is a side view of the washer, with the washer having a contoured bone-engagement surface complimentary to the shape of a bone, according to one embodiment;

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure. Also, like reference numbers (e.g., 112 and 212) refer to like components (e.g., different embodiments of the same component).

Illustrated in FIGS. 1A-4B are several representative embodiments of a washer for supporting a cable extending from a hole (e.g., a tunnel, passage, or passageway) in a bone, As described herein, the washer for supporting the cable provides various advantages and benefits over other medical tools and procedures. However, the recited advantages are not meant to be limiting in any way, as one skilled in the art will appreciate that other advantages may also be realized upon practicing the present disclosure.

Figure 1A:
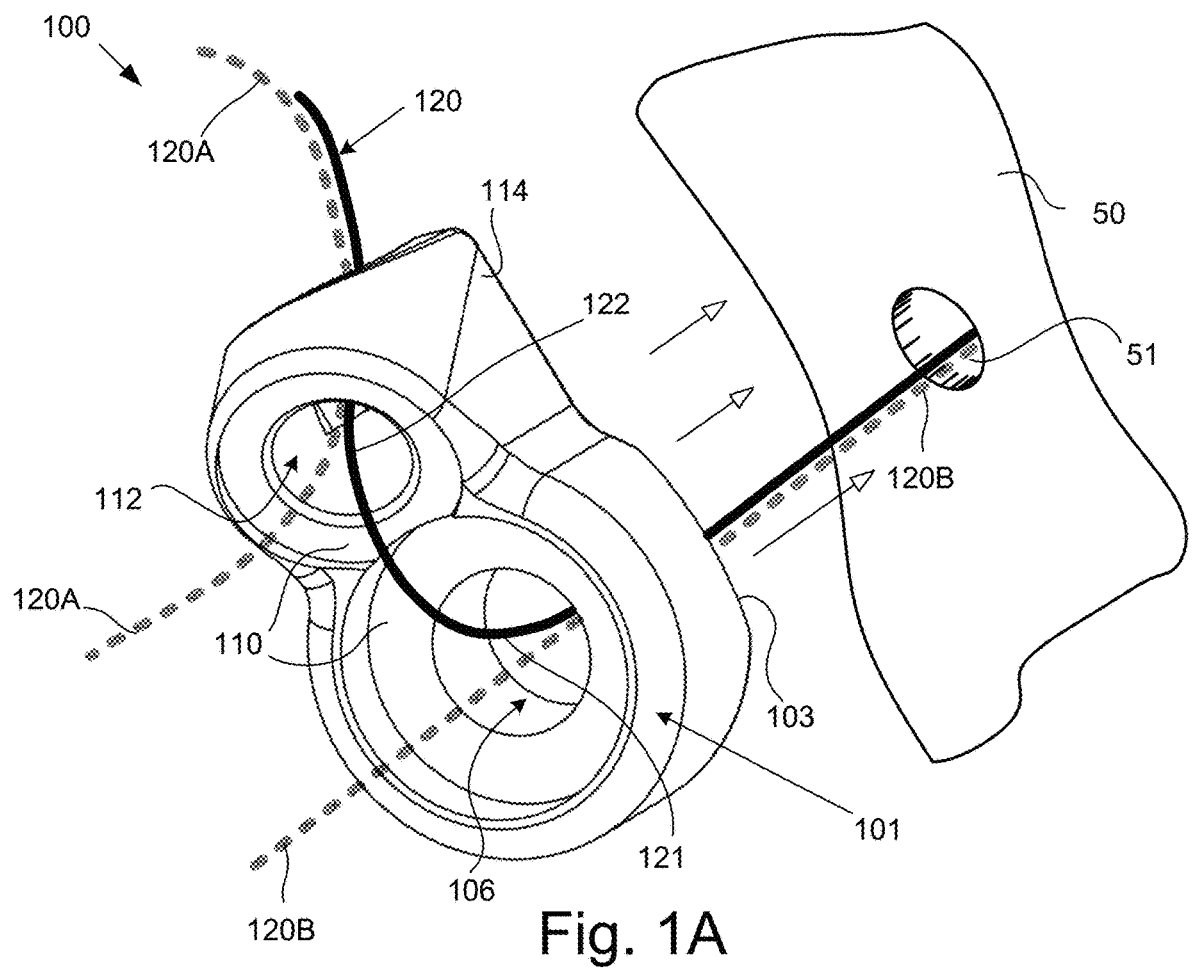
FIG. 1A is a top perspective view of a washer for supporting a cable extending from a hole in a bone, with the washer having a pass-through aperture and a channel, according to one embodiment.
Figure 1B:
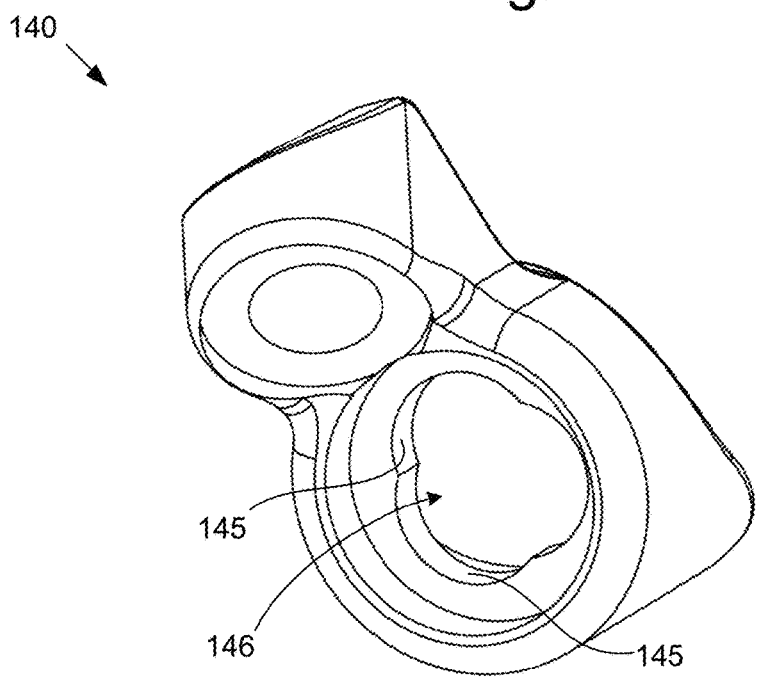
FIG. 1B is a top perspective view of another embodiment of the washer for supporting a cable extending from a hole in a bone, with the washer having a non-circular pass-through aperture.

FIG. 1A is a top perspective view of the washer 100 for supporting a cable 120 extending from a hole 51 in a bone 50, according to one embodiment. The washer 100 includes a bone-engaging surface 103 and a cable-engaging surface 110 opposing the bone-engaging surface 103. The washer 100 further includes a pass-through aperture 106 extending through the washer 100 and a channel 112 extending through the washer 100. The extension direction of the pass-through aperture 106 is along a first axis 107 (FIG. 1C) and the extension direction of the channel 112 is along a second axis 113 that is at least one of non-parallel to or offset from the first axis 107. In one embodiment, the channel 112 extends from a location proximate the pass-through aperture 106. The pass-through aperture 106 of the washer 100 in FIG. 1A has a substantially circular cross-section. According to another embodiment, as depicted in FIG. 1B, the pass-through aperture 106 of the washer 140 has a non-circular cross-section. For example, sidewalls 145 of the pass-through aperture 106 can form a lobed-shape (e.g., three lobes), thus allowing greater flexibility when positioning the washer 140 over the hole 51 in the bone 50.

The washer 100 is configured to be positioned directly adjacent (e.g., abutting) the bone 50 so as to cover the hole 51 in the bone 50. For depiction clarity, the washer 100 in FIG. 1A is shown a distance removed from the bone 50, but directional arrows indicate how the washer 100, during use, will be positioned to directly contact the surface of the bone 50 proximate the hole 51. The cable 120 extends from the hole 51 and passes through the pass-through aperture 106, across the cable-engaging surface 110, and through the channel 112. A first portion 121 of the cable 120 is disposed in the pass-through aperture 106 and a second portion 122 of the cable 120 is disposed in the channel 112. In this manner, the washer 100 is configured to redirect the cable 120 after extending out from the hole 51.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 120 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 120 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. Because the cable 120 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 120 to be tensioned to a measurable and adjustable tension improves the reliability and reproducibility of surgical procedures when compared with other medical procedures that do not utilize cables. The cable 120 may be made from any one of various materials. For example, in specific implementations, the cable 120 is made from metal, such as stainless steel, titanium, or other metal.

As introduced above in the Background section, cables can be used to suture torn tissue back together and/or to hold bone fragments securely in place. For example, one end of a cable may be anchored to a bone while the other end of the cable is wrapped around the bone to provide external reinforcement after the fractured bone has been set (e.g., a cerclage configuration). In another example, a cable may be used to couple the bone to a soft-tissue segment or to another bone. The washer 100 described herein is specifically configured to engage and support a cable 120 as it changes directions upon extending from a hole 51 in a bone 50. In other words, the washer 100 facilitates a change in the direction of the cable 120 by mitigating wear and damage to the bone 50 that would otherwise occur if the washer 100 were not employed. Also, cables may be tensioned in order to adequately hold the various tissues in place. Accordingly, if the washer 100 was not employed to cover the hole 51, the tensioned cable, extending in a different direction upon exiting the hole 51, would potentially cut into the edge of the bone defining the hole 51, causing the patient to experience pain and/or causing the surgery to be compromised as the cable loses tension, cuts through the bone, or fractures the bone. In other words, the washer 100 prevents the cable 120 from directly contacting and potentially damaging the edge of the hole 51 in the bone 50 and also engages the cable 120 within the channel 112 to direct and retain the cable 120 in a desired direction (e.g., across the surface of the bone).

In order for the cable 120 to be tensioned, the opposing end of the cable (e.g., the end of the cable that extends into the hole 51 of the bone 50) must be anchored or securely retained. In one embodiment, the cable 120 is coupled to a bone anchor that has been installed in the hole 51 or on an opposite side of the bone 50. In another embodiment, the opposing end of the cable 120 has a stop, such as a crimp body, that is engageable with the opposing surface of the bone proximate the opposite opening of the hole, thus preventing the cable 120 from sliding through the hole in the bone 50 and thereby ensuring that the cable 120 remains securely anchored.

In another embodiment, two separate cables 120A, 120B (depicted as dashed lines) each extends through a respective one of the pass-through aperture 106 and the channel 112. In such an embodiment, to retain the cables 120A, 120B in place relative to the washer 100, a crimp body (not shown) may be crimped to each of the cables 120A, 120B. The crimp body can be configured to engage the cable-engaging surface 110 of the washer 100 (e.g., nestably engage or be seated onto the cable-engaging surface 110), thereby retaining the cables 120A, 120B in place relative to the washer 100. In one implementation, the cable 120B is retained on the washer 100 and extends through the hole 51 in the bone 50, and the cable 120A is retained on the washer 100 and extends around (e.g., to cerclage) the bone 50. In yet another implementation, one end of a cable can extend through the hole 51 in the bone 50 and the pass-through aperture 106, and be retained to the washer 100 by a crimp body, and another end of the same cable can wrap around the bone 50, pass through the channel 112, and be retained to the washer 100 by a separate crimp body.

As described above, the pass-through aperture 106 of the washer 100 extends along the first axis 107 and the channel 112 extends along the second axis 113. The channel 112 is specifically configured to direct the cable 120 in a specific direction and prevent the cable from inadvertently slipping laterally across the surface of the bone 50.

According to the depicted embodiment, the first and second axes 107, 113 are non-parallel. In one embodiment, the first axis 107 is perpendicular to the second axis 113. In another embodiment, a minor angle between the first axis 107 and the second axis 113 is less than 45 degrees. In yet another embodiment, the minor angle between the first axis 107 and the second axis 113 is about 30 degrees. In another embodiment, the angle between the first axis 107 and the second axis 113 may be dependent on the configuration and dimensions of the bone (e.g., the angle between the first and second axes may be greater than 90 degrees).

As described above, the pass-through aperture 106 and the channel 112 extend along the first axis 107 and second axis 113, respectively. The washer 100 may be configured to have a specific angle between the first and second axes 107, 113 that corresponds with the specific dimensions of the bone 50 and that corresponds with the desired extension direction of the cable 120 after it exits the hole 51 of the bone 50. Nevertheless, despite a practitioner's intent to match the desired extension direction of the second portion 122 of the cable 120 with the second axis 113 of the channel 112, the direction of the cable and the second axis 113 may not be parallel. In other words, the extension directions of the first and second portions 121, 122 of the cable 120 are not necessarily parallel with the first and second axes 107, 113 of the pass-through aperture 106 and the channel 112. For example, the first portion 121 of the cable 120 may extend at an angle relative to the first axis 107 through the pass-through aperture 106 and/or the second portion 122 of the cable 120 may extend at an angle relative to the second axis 113 of the cable 120 through the channel 112. The extent of the offset between the extension direction of the cable and the first and second axes may be based on the relative sizes of the diameter of cable 120 and the cross-sectional dimensions of the pass-through aperture 106 and channel 112.

The cable-engaging surface 110 is the portion of the washer 100 upon which the cable 120 is directly engaged as it transitions between the pass-through aperture 106 and the channel 112. The cable-engaging surface 110 may be smooth and/or have rounded edges and corners to prevent wear on the cable 120. In one embodiment, as described in greater detail below with reference to FIGS. 4A and 4B, the cable-engaging surface 110 may have a groove that further facilitates the proper and secure engagement between the cable 120 and the washer 100.

The bone-engaging surface 103, opposite the cable-engaging surface 110, is the portion of the washer 100 that directly contacts the bone 50. In one embodiment, the cable-engaging surface and the bone-engaging surface are substantially parallel. In another embodiment, the bone-engaging surface 103 is substantially coplanar. In yet another embodiment, the bone-engaging surface 153 may be specifically shaped and designed to conform to and/or complement the surface shape of the bone 50 upon which it is engaged. For example, the side view of the washer 150 in FIG. 1D shows the bone-engaging surface 153 having undulations or indents that correspond with a specific shape of the bone against which the washer 150 will be positioned.

The footprint of the washer 100, according to the depicted embodiments, is non-circular. In other words, the washer may include an arm 114 extending radially outward away from a main body 101 of the washer, through which the pass-through aperture 106 extends, with the channel 112 extending from proximate the pass-through aperture through the arm 114. Also, according to the depicted embodiment, at least a portion of the channel 112 is circumferentially closed. In another embodiment, the channel may be open (i.e., only partially circumferentially closed) as described in greater detail below with reference to FIGS. 4A and 4B.

Figure 2A:
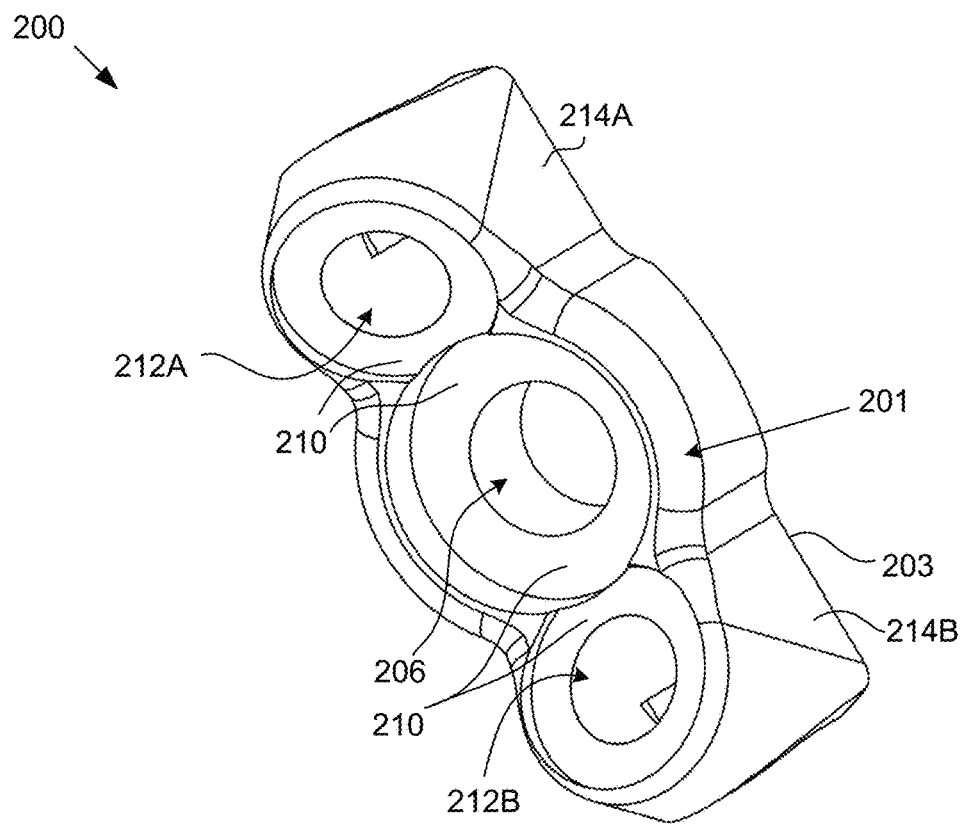
FIG. 2A is a top perspective view of the washer, with the washer having two channels, according to one embodiment.
Figure 2B:
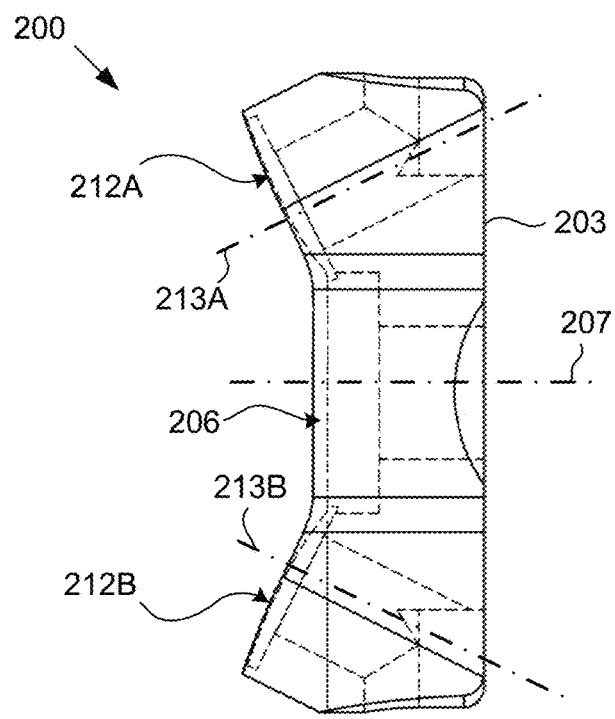
FIG. 2B is a side view of the washer of FIG. 2A, according to one embodiment.
Figure 2C:
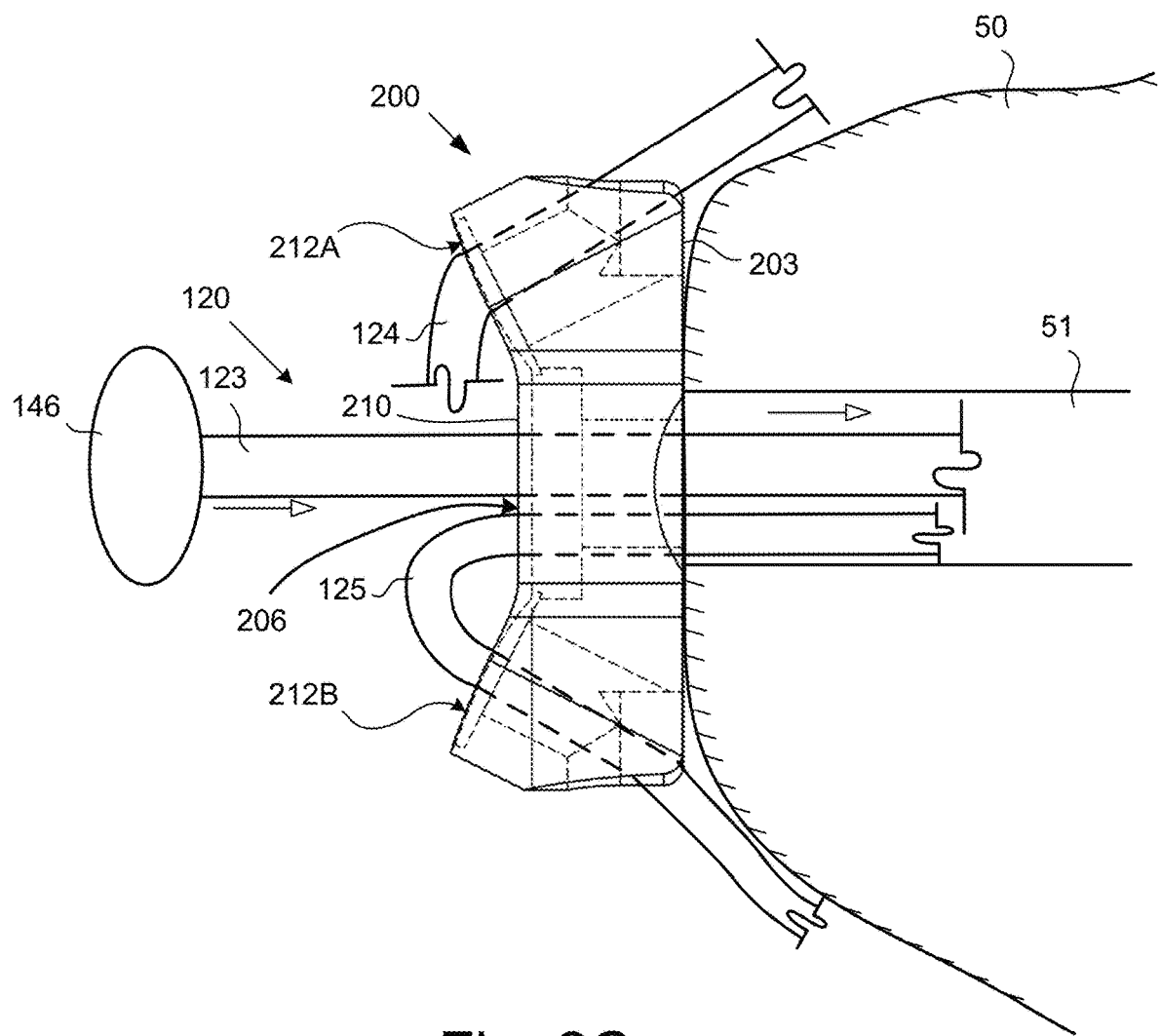
FIG. 2C is a side view of the washer of FIG. 2A showing a first portion of the cable having an affixed stop that seats against the cable-engaging surface of the washer; according to one embodiment.
Figure 2D:
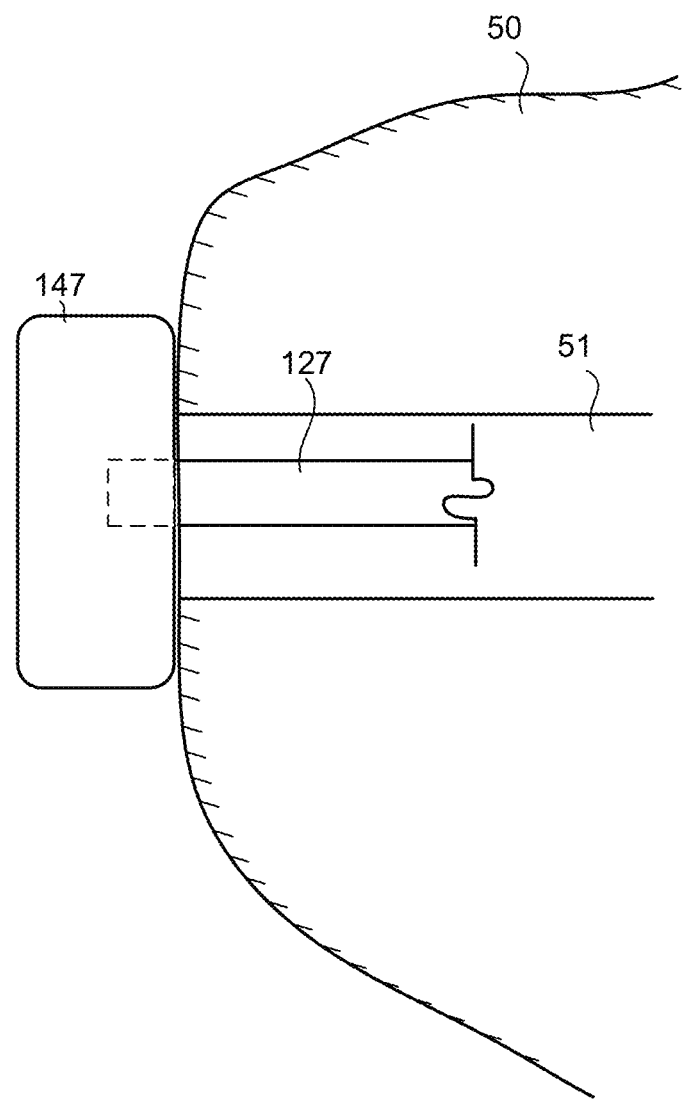
FIG. 2D is a schematic side view of a stop having a cable pre-attached to the stop.
Figure 3:
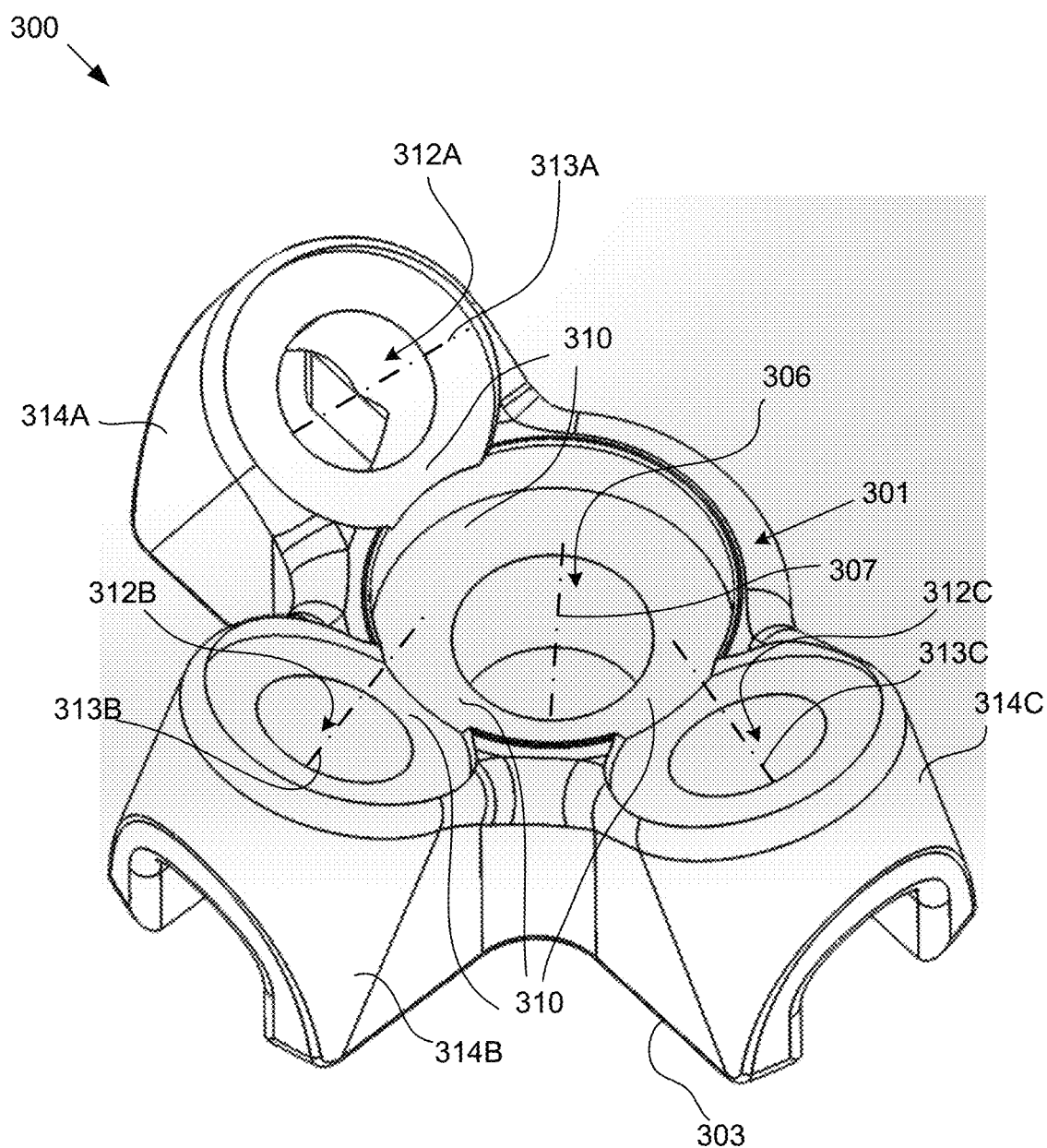
FIG. 3 is a top perspective view of the washer, with the washer having three channels, according to one embodiment.

FIGS. 2A-3 show various embodiments of the washer having multiple channels. More specifically, FIGS. 2A and 2B show a top perspective view and a side view, respectively, of one embodiment of the washer 200 with two channels 212A, 212B while FIG. 3 shows a top perspective view of the washer 300 with three channels 312A, 312B, 312C.

The washer 200 in FIGS. 2A and 2B has the pass-through aperture 206 disposed in between the two arms 214A, 214B, each arm having one of the channels 212A, 212B. In one embodiment, the two axes 213A, 213B of the channels 212A, 212B extend in mirror image directions (i.e., both angles are the same relative to the first axis 207 of the pass-through aperture 206). In another embodiment, however, the two axes 213A, 213B of the channels 212A, 212B extend in different directions relative to the first axis 207 of the pass-through apertures 206. In other words, the first channel 212A on the first arm 214A of the washer 200 may be configured to extend the cable in a direction, relative to the first axis 207, that is different than the second channel 212B in the second arm 214B of the washer 200 based on the specific dimensions and shape of the bone 50.

FIG. 2C is a side view of the washer 200 of FIG. 2A showing a first portion 123 of the cable 120 having a stop 146 affixed to an end of the cable 120. The stop 146 is configured to seat against the cable-engaging surface 210 of the washer 200. The direction arrows in FIG. 2C show the direction the cable 120 is pulled through the pass-through aperture 206 of the washer 200 to move the stop 146 into seated engagement with the washer 200. After a portion of the cable is passed through the pass-through aperture 206 of the washer 200, the portion of the cable 120 may be passed through a hole in the bone and/or wrapped around bone. A pulling force may be exerted on the cable 120 to tension the cable 120 to a measureable tension. Furthermore, after passing through a hole in the bone and tensioned, a free end of the cable 120 can be locked and/or crimped to retain the tension in the cable. In some implementations, the pass-through hole 51 extends through two bone segments of a fractured bone such that tensioning the cable 120 to a measurable and adjustable tension in this manner causes the two bone segments to compress together with a measurable and adjustable compression. Moreover, because the cable 120 passes through the bone, as opposed to around the bone, the compression of the two bone segments is applied in one direction (e.g., unidirectionally) concentric with the cable 120, to more uniformly and evenly distribute the compressive load to the bone segments, as opposed to multiple directions when compression is applied by a cable passing around the bone.

As defined herein, a stop is any of various features, such as nuts, clips, conventional washers, pins, balls, caps, lids, or the like, that are attachable to a cable and capable of engaging an opening (e.g., a surface adjacent to or defining the opening) to prevent further passage of the cable through the opening. In one embodiment, the stop 146, shown schematically in FIG. 2C, is spherical or rounded. In another embodiment, the stop 146 resembles a flange or conventional washer, and has a shape that complements the shape of the cable engaging surface 210 of the washer 200 such that the stop 146 is configured to nestably engage the washer 200. According to yet another embodiment, the stop 146 is at least partially deformable to compliment the shape of the cable-engaging surface 210 of the washer 210 as the cable 120 is tensioned.

The stop 146 can be integrated into or permanently attached to a first end portion 123 of the cable 120. For example, the stop 146 may be swaged, crimped, welded, bonded, or otherwise fixedly secured to the cable 120. In another embodiment, the stop 146 can be detachably coupled to the cable 120, thus allowing for stops with different shapes, dimensions, angles, etc. to be alternatively coupled to the same cable as desired.

Referring again to FIG. 2C, after or prior to the cable 120 being passed through the washer 200 and the stop 146 seating on the washer 200, other cables, such as cable 124, 125, can pass through any of the channels or aperture of the washer 200 such that the washer can be used to redirect other cables passing through or around the bone. Alternatively, after passing through the hole in the bone, the cable 120 may wrap around or pass back through the hole in the bone to again engage and be redirected by the washer 200 (e.g., the representations of the cable 124, 125 could be opposing ends of the cable 120 after the cable 120 has passed through the hole in the bone in the direction indicated).

FIG. 2D is a schematic side view of a stop 147 having a cable 127 pre-attached. In one embodiment, the stop 147 has a cross-sectional dimension that is larger than the diameter of the hole 51 in the bone 50, thereby preventing the stop 147 from passing through the hole 51. In one embodiment, the stop 147 is a disk-like stop, analogous to the stop 146 described above. For example, the stop 147 can directly engage the surface of the bone 50 or the stop 147 can be seated in a separate washer that is analogous to the washers described herein. In another embodiment, the stop 147 has features that are analogous to the washers described herein, but with a pre-attached cable 127.

The washer 300 in FIG. 3 has three arms 314A, 314B, 314C extending radially outward from the main body 301 of the washer 300, with three channels 312A, 312B, 312C that all extend along non-parallel axes 313A, 313B, 313C relative to the first axis 307 of the pass-through aperture 306. The bone-engaging surface 303 of the arms 314A, 314B, 314C of the washer 300 may be substantially co-planar with each other but may extend outward away from the pass-through aperture 306 at 90 degrees from each other (thereby leaving 180 degrees between two of the arms 314A, 314B, 314C). In another embodiment, the arms 314A, 314B, 314C are still substantially coplanar but are equally spaced apart in their extension directions (i.e., 120 degrees between adjacent arms). In yet another embodiment, the arms 314A, 314B, 314C are not coplanar, with one arm having a different relative elevation in order to complement the shape of the surface of the bone 50. For example, the arms 314A, 314B, 314C may have different relative vertical elevations and/or the arms 314A, 314B, 314C may be contoured to complement to a specific shape/dimension of a bone.

In another embodiment, four or more arms, each with its own channel, may extend outward away from the main body of the washer, through which the pass-through aperture extends. Alternatively, the washer may include multiple pass-through apertures with multiple arms extending from each pass-through aperture. In other words, the washer may resemble a panel that is configured to span a comparatively larger span of bone surface for a more extensive surgical procedure. In one embodiment, one or more cables may be pre-attached to the washer, as described above with reference to FIG. 2D.

Figure 4A:
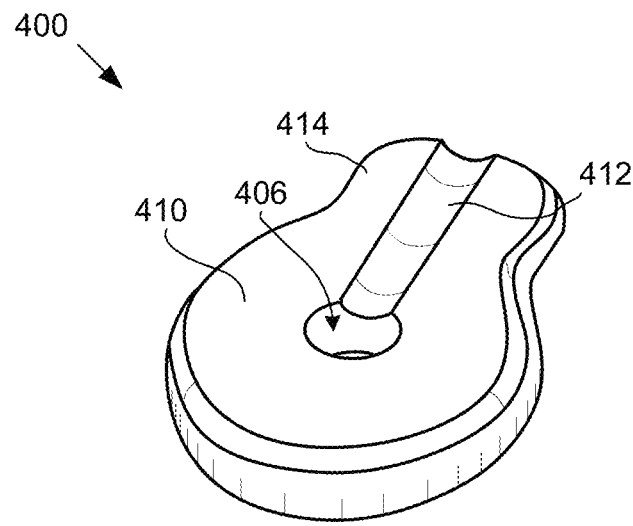
FIG. 4A is a top perspective view of the washer, with the channel of the washer being a groove in the cable-engaging surface extending to a peripheral edge of the washer, according to one embodiment.

FIG. 4A is a top perspective view of the washer 400, with the groove 412 of the washer being an open groove in the cable-engaging surface 410 extending to a peripheral edge of the washer 400. In such an embodiment, with the cable received within the groove 412, the cable is prevented from moving laterally but is not prevented from slipping out of engagement with the groove 412 if the cable experiences an upward away force, relative to the cable-engaging surface, that moves the cable out of the groove 412.

Figure 4B:
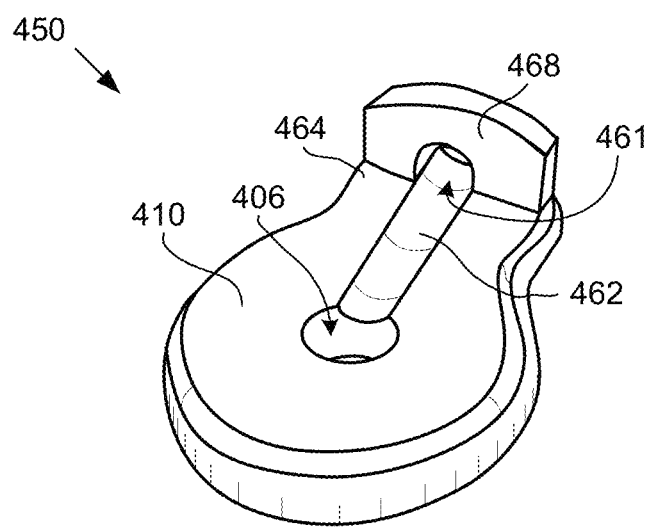
FIG. 4B is a top perspective view of the washer, with a portion of the channel of the washer being circumferentially closed, according to one embodiment.

FIG. 4B is a top perspective view of the washer 450, with a portion 468 of the groove 462 of the washer 450 being circumferentially closed. In such an embodiment, the circumferentially closed portion 468 is a protruding lip extending away from the cable-engaging surface 410. In one embodiment, the circumferentially closed portion 468 of the groove 462 includes a crimping mechanism that enables the cable passing through circumferentially closed portion to be crimped and secured to the washer 450. In one embodiment, the circumferentially closed portion 468 is not disposed near the edge of the washer 450 but instead is disposed comparatively closer to the aperture 406 or alternatively spans the entire length of the groove 462.

Figure 5:
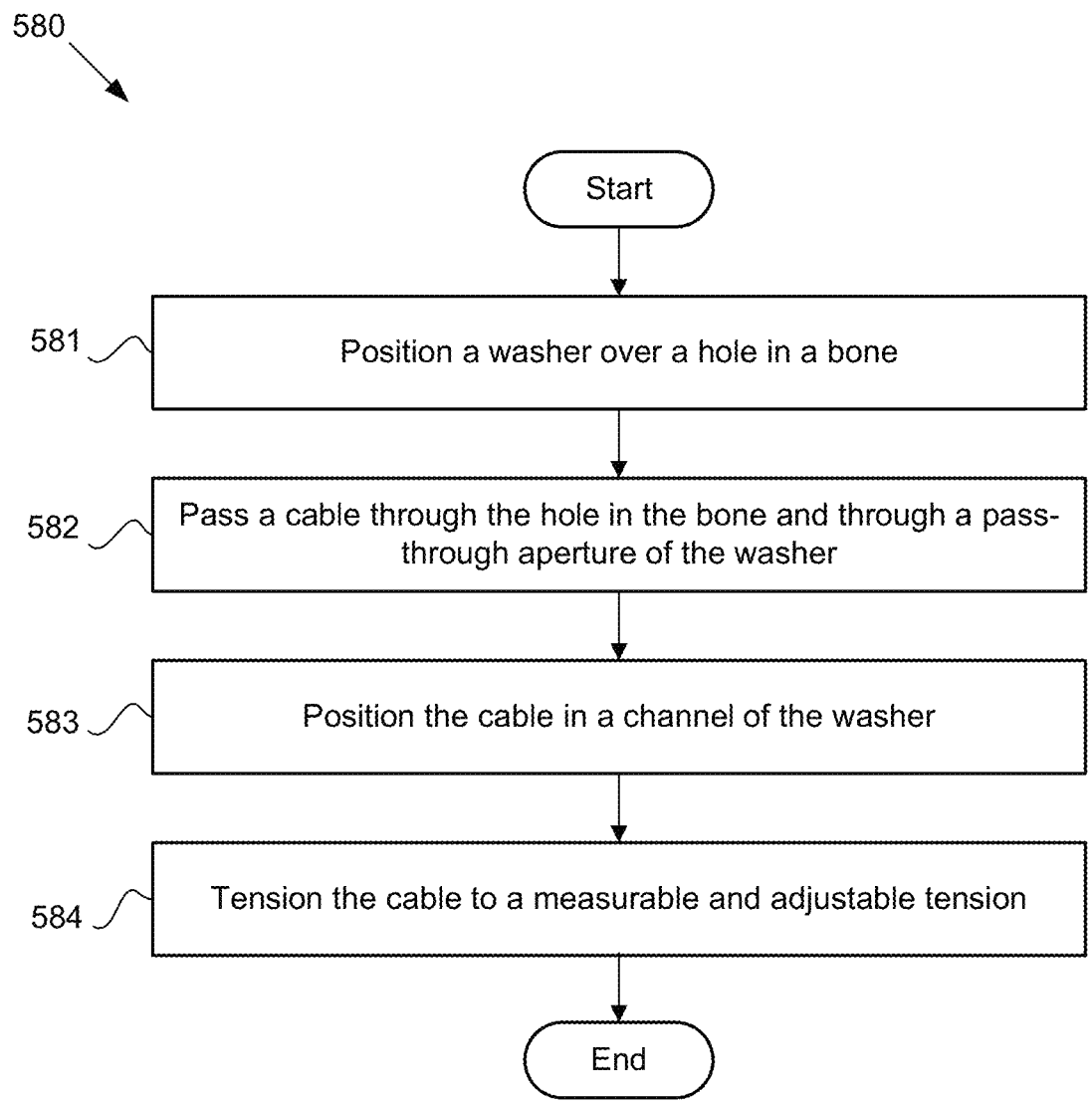
FIG. 5 is a schematic flowchart diagram of a method using the washer to support a cable extending from a hole in a bone.

FIG. 5 is a schematic flowchart diagram of one embodiment of a method 580 for using the washer to support a cable extending from the bone. The method 580 includes positioning the washer over the hole in the bone such that the bone-engaging surface of the washer engages the surface of the bone adjacent the hole at 581. The method 580 further includes passing the cable through the hole in the bone and through the pass-through aperture in the washer extending along a first axis from the bone engaging surface to a cable-engaging surface at 582. Still further, the method 580 includes positioning the cable in the channel of the washer with the channel extending along a second axis that is at least one of non-parallel to or offset from the first axis at 583.

In one embodiment, positioning the cable in the channel includes passing the cable through a circumferentially closed portion of the channel. In such a configuration, the method 580 further includes crimping the cable in the circumferentially closed portion of the channel. The method 580 also includes tensioning the cable, to a measurable and adjustable tension, after passing the cable through the hole in the bone and after positioning the cable in the channel of the washer at 584, to cause a measurable and adjustable compression of the bone by the cable in some implementations. In one embodiment, the method 580 may further include releasing and re-tensioning the cable to the same or a different measurable and adjustable tension.

Figure 6:
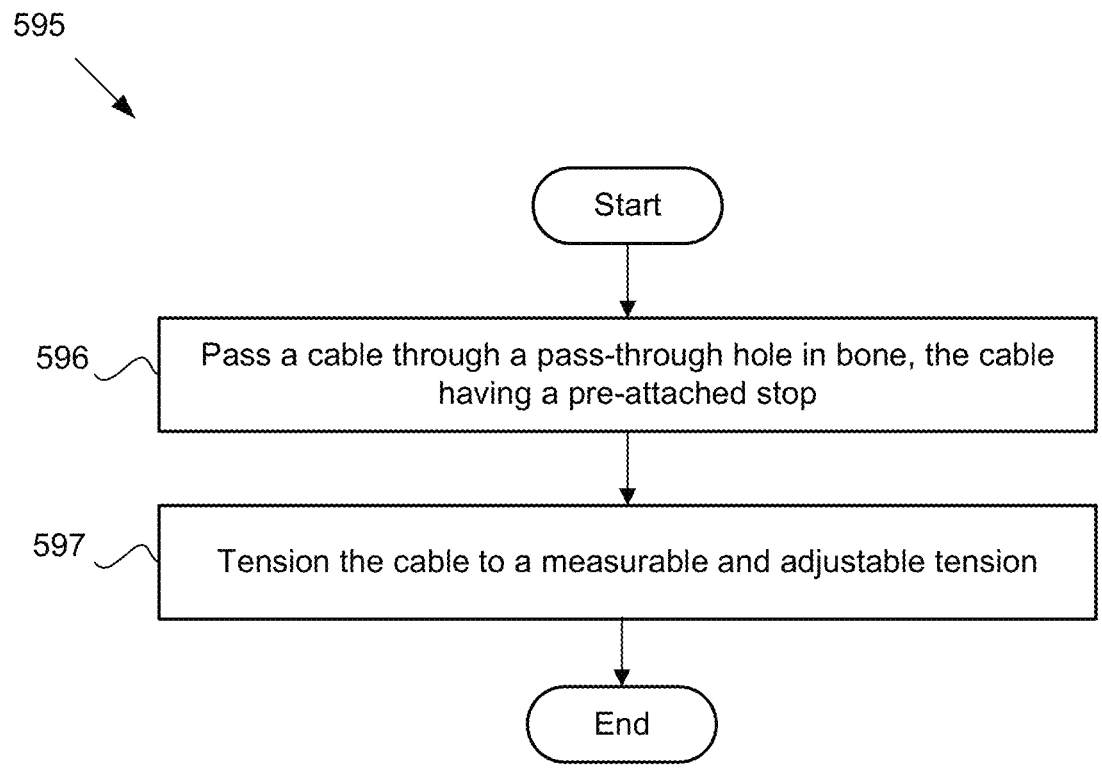
FIG. 6 is a schematic flowchart diagram of one embodiment of a method for extending a cable through a pass-through hole in a bone.
Figure 7:
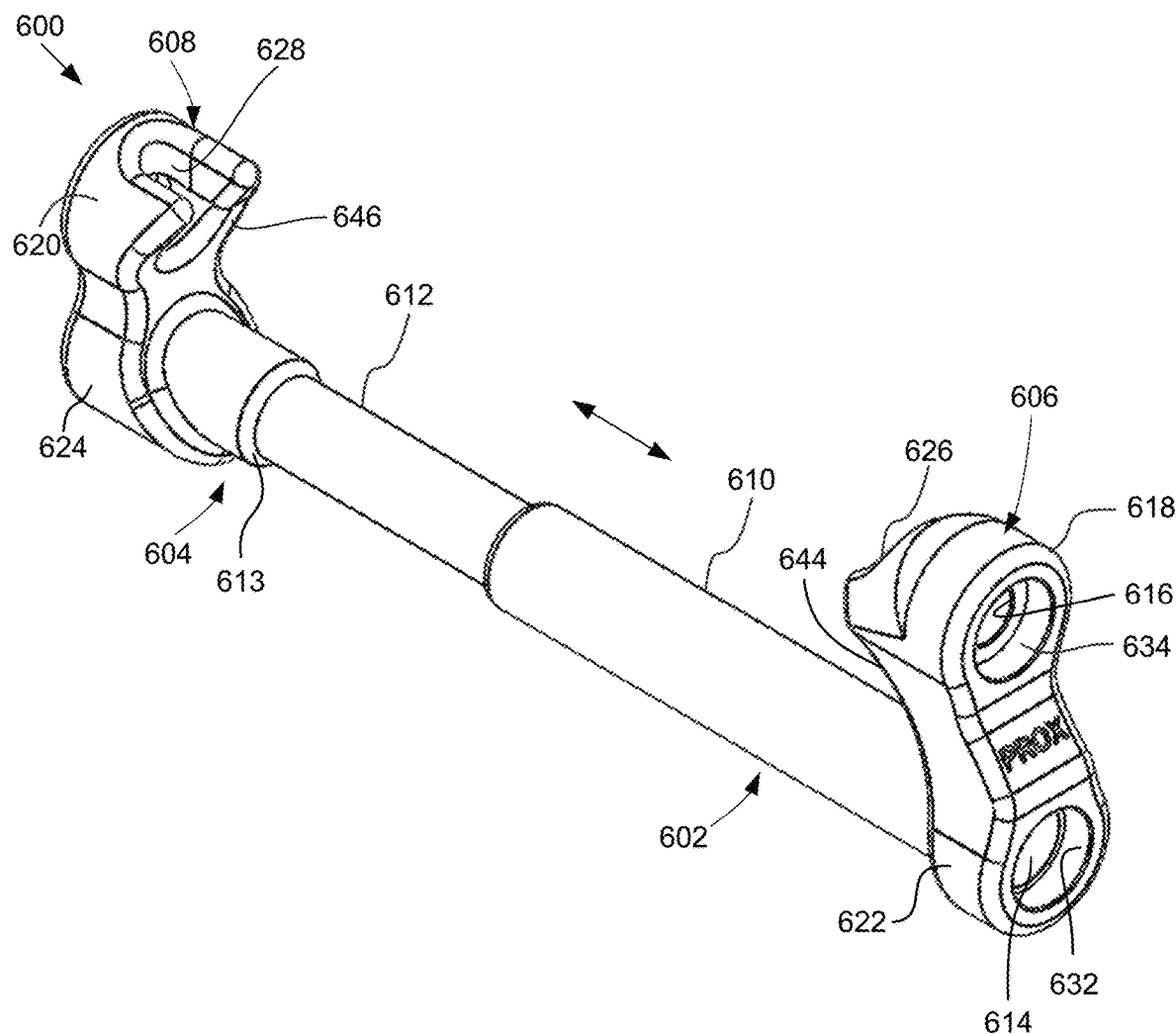
FIG. 7 is a perspective view of a washer assembly, shown with a first length, according to one or more embodiments of the present disclosure.
Figure 8:
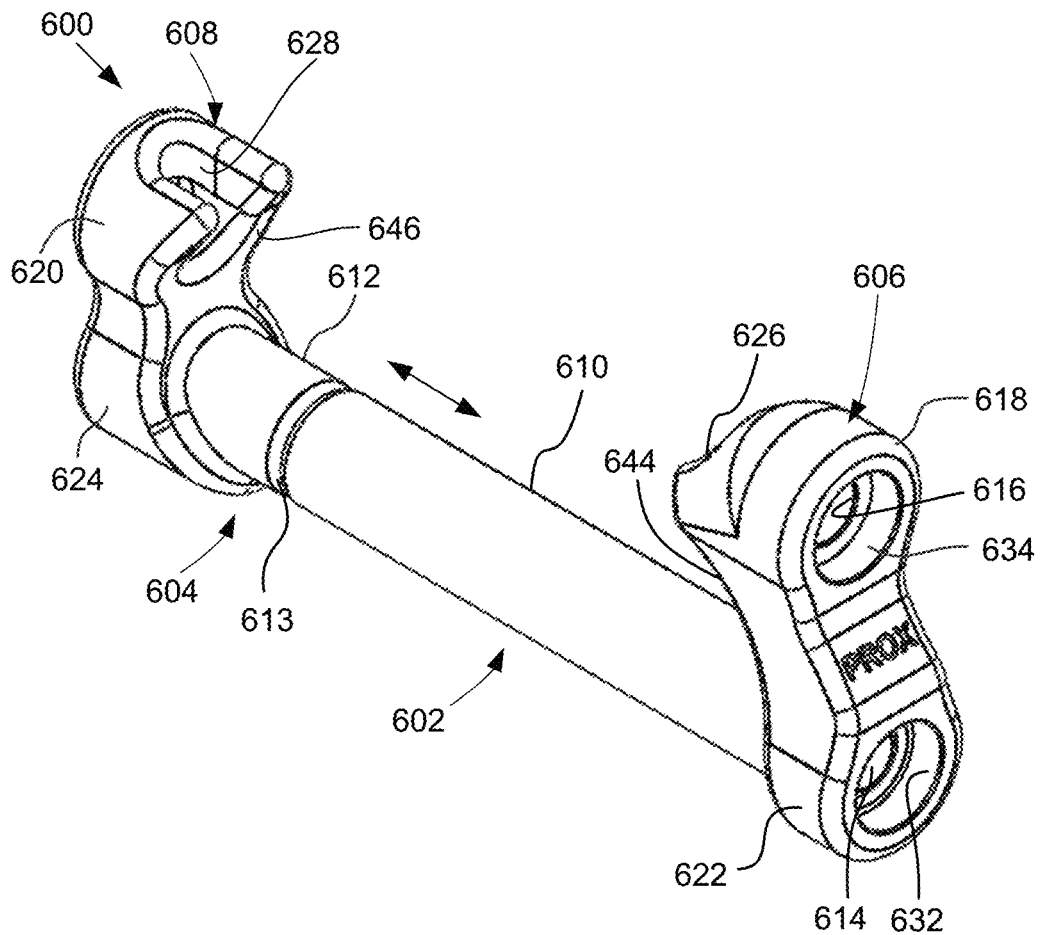
FIG. 8 is a perspective view of the washer assembly of FIG. 7, shown with a second length shorter than the first length, according to one or more embodiments of the present disclosure.
Figure 9:
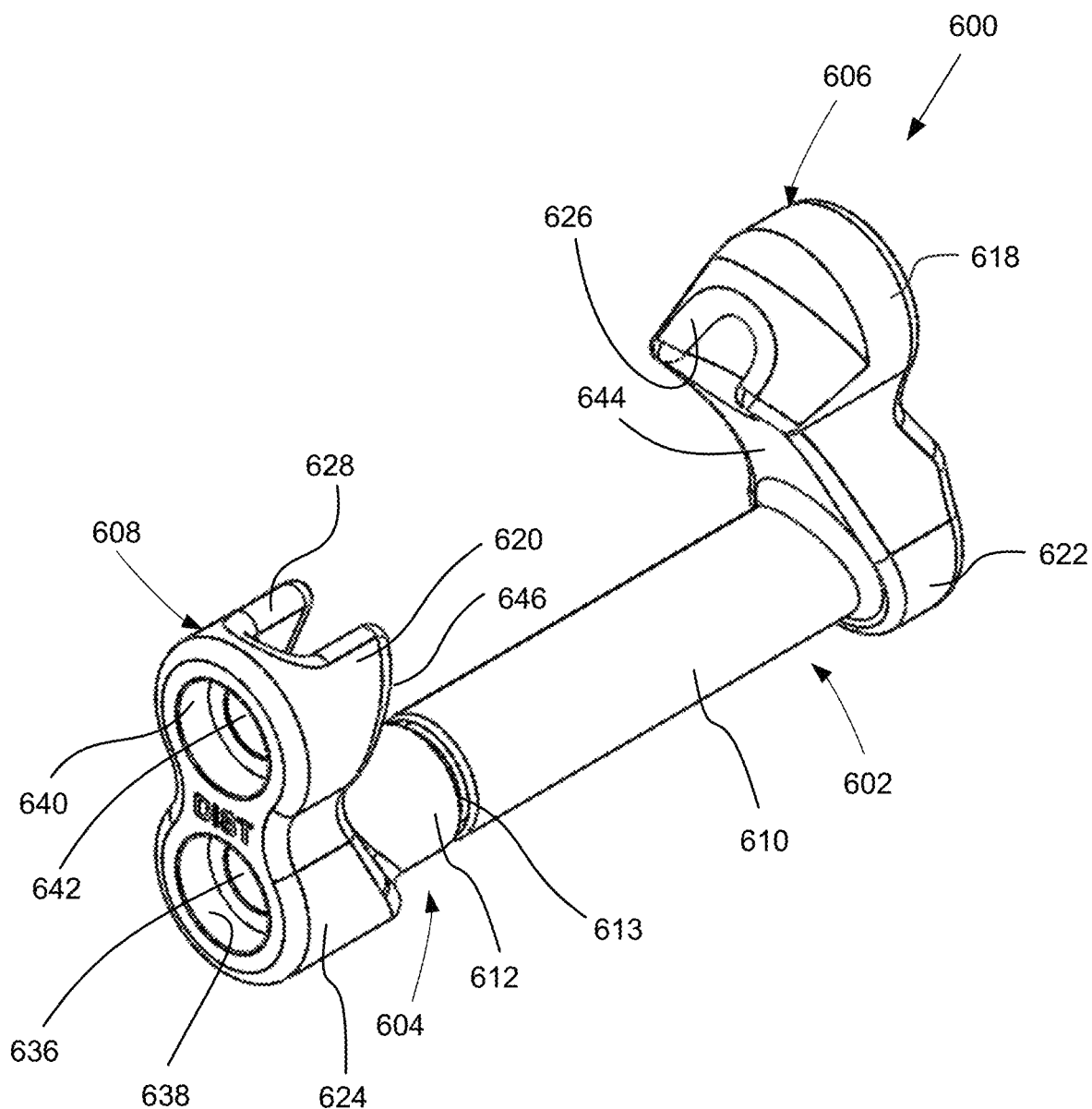
FIG. 9 is an alternative perspective view of the washer assembly of FIG. 7, shown with the second length, according to one or more embodiments of the present disclosure.
Figure 10:
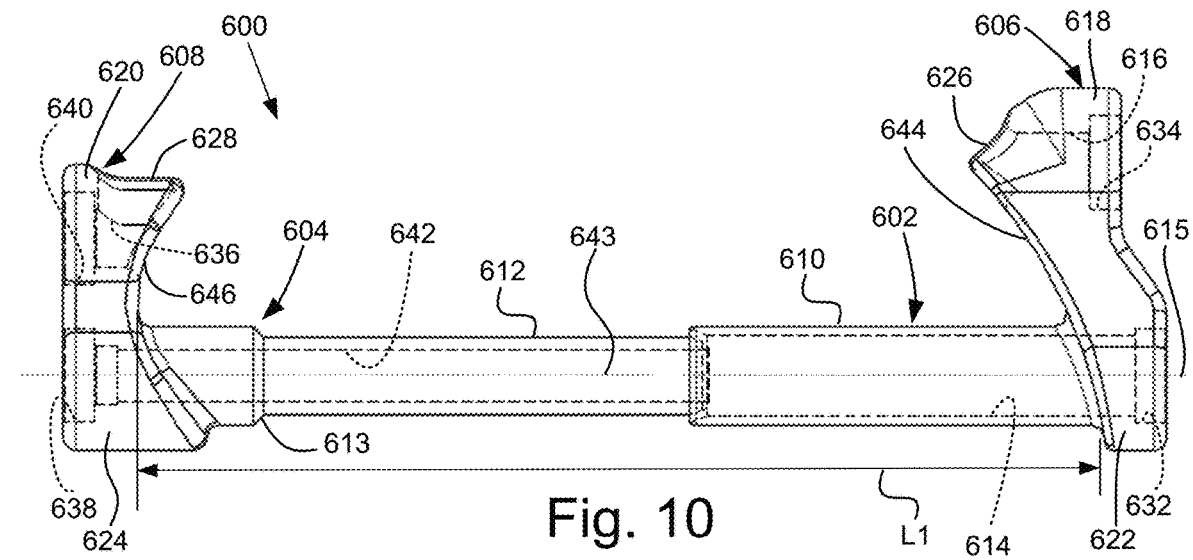
FIG. 10 is a side elevation view of the washer assembly of FIG. 7, shown with the first length, according to one or more embodiments of the present disclosure.
Figure 11:
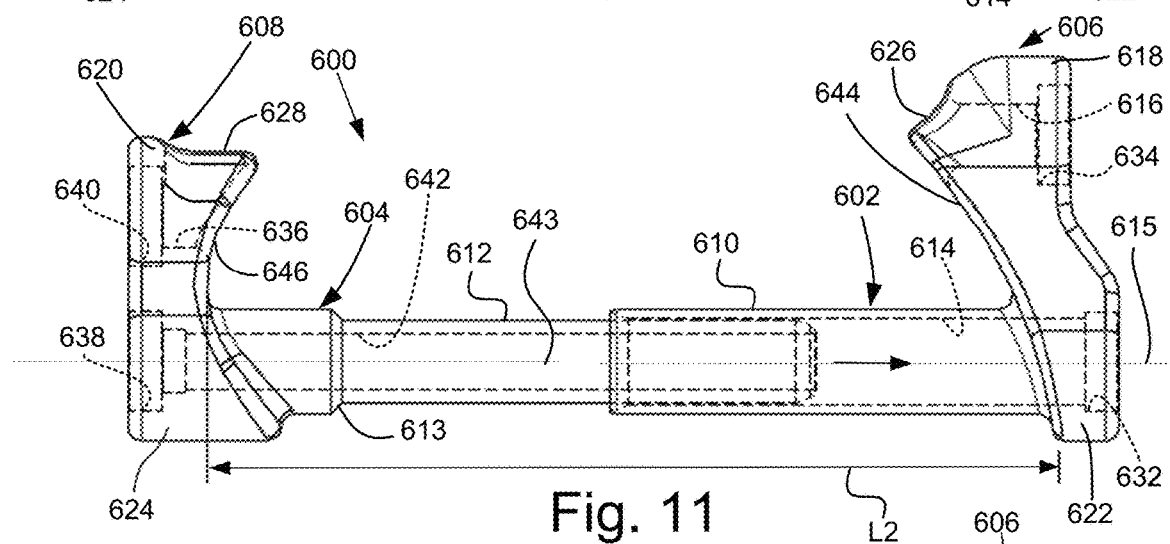
FIG. 11 is a side elevation view of the washer assembly of FIG. 7, shown with a third length less than the first length and more than the second length, according to one or more embodiments of the present disclosure.
Figure 12:
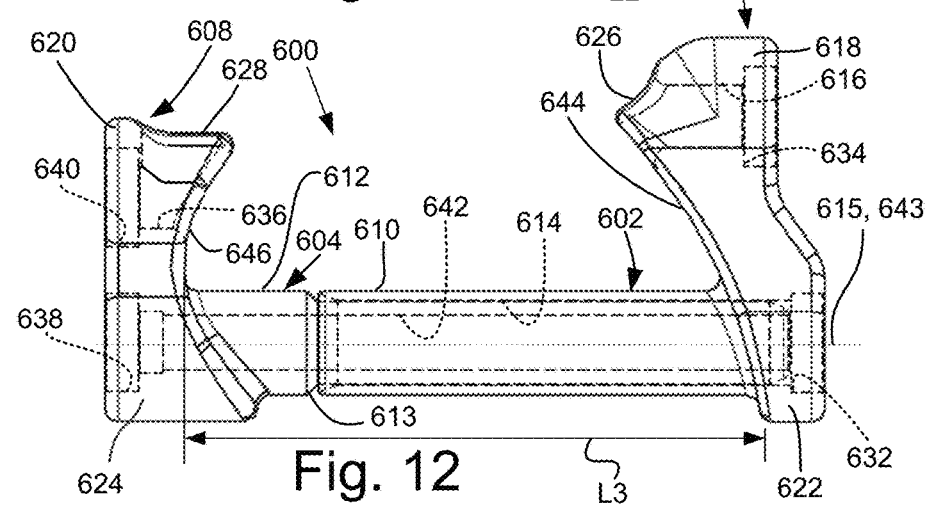
FIG. 12 is a side elevation view of the washer assembly of FIG. 7, shown with the second length, according to one or more embodiments of the present disclosure.

FIG. 6 is a schematic flowchart diagram of one embodiment of a method 595 for extending a cable through a pass-through hole in a bone. The method 595 includes passing a cable through the pass-through hole in the bone, with the cable having a stop that is pre-attached at 596. The method 595 further includes tensioning the cable to a measurable and adjustable tension and 597, to cause a measurable and adjustable compression of the bone by the cable in some implementations. In one embodiment, before tensioning the cable, the method 595 further includes positioning a washer over the pass-through hole in the bone so that a bone-engaging surface of the washer engages a surface of the bone adjacent the pass-through hole and passing the cable through a pass-through aperture in the washer extending along a first axis from the bone engaging surface to a cable-engaging surface. The method further may include seating the stop against a complimentary shape of the cable-engaging surface of the washer (e.g. as described above with reference to FIG. 2C). In one implementation, the stop is a washer and the method 595 further includes redirecting one or more additional cables or an opposite end portion of the cable across a cable-engaging surface of the washer.

As mentioned above with reference to method 580, method 595 may optionally include, after the cable is tensioned to a measurable and adjustable tension, releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

In some situations, tensioning the cable to a measurable and adjustable tension to impart a measurable and adjustable compression of the bone by the cable through the use of washers may affect the positioning of the washers and potentially cause damage to the bone. For example, for certain bones, such as those with relatively soft cortical tissue, and for certain placements of washers on bones, such as on relatively flat surfaces of bones, tensioning the cable may cause one or more of the washers to move or shift and, in some cases, cause the cable to cut into the outer cortical tissue of the bone.

Referring now to FIGS. 9-12, one embodiment of a washer assembly 600, for supporting at least one cable extending at least one of around a bone or through a pass-through hole formed in the bone, is shown. The washer assembly 600 and at least one coupling element (e.g., at least one of cables 660A, 660B) form a system 601 (see, e.g., FIG. 13) that can be used to reduce and stabilize at least one of a fracture in, a dislocation of, or a subluxation of at least one bone. In some implementations, the washer assembly 600 helps to prevent movement of washers on and cable-induced damage to bones when the cable of the system is tensioned. The washer assembly 600 includes a first portion 602 and a second portion 604. The first portion 602 and the second portion 604 are physically engaged to form the washer assembly 600. The coupling element is formed separate from the first portion 602 and the second portion 604 and is releasably and detachably coupled to and reversibly decouplable from the first portion 602 and the second portion 604.

Figure 13:
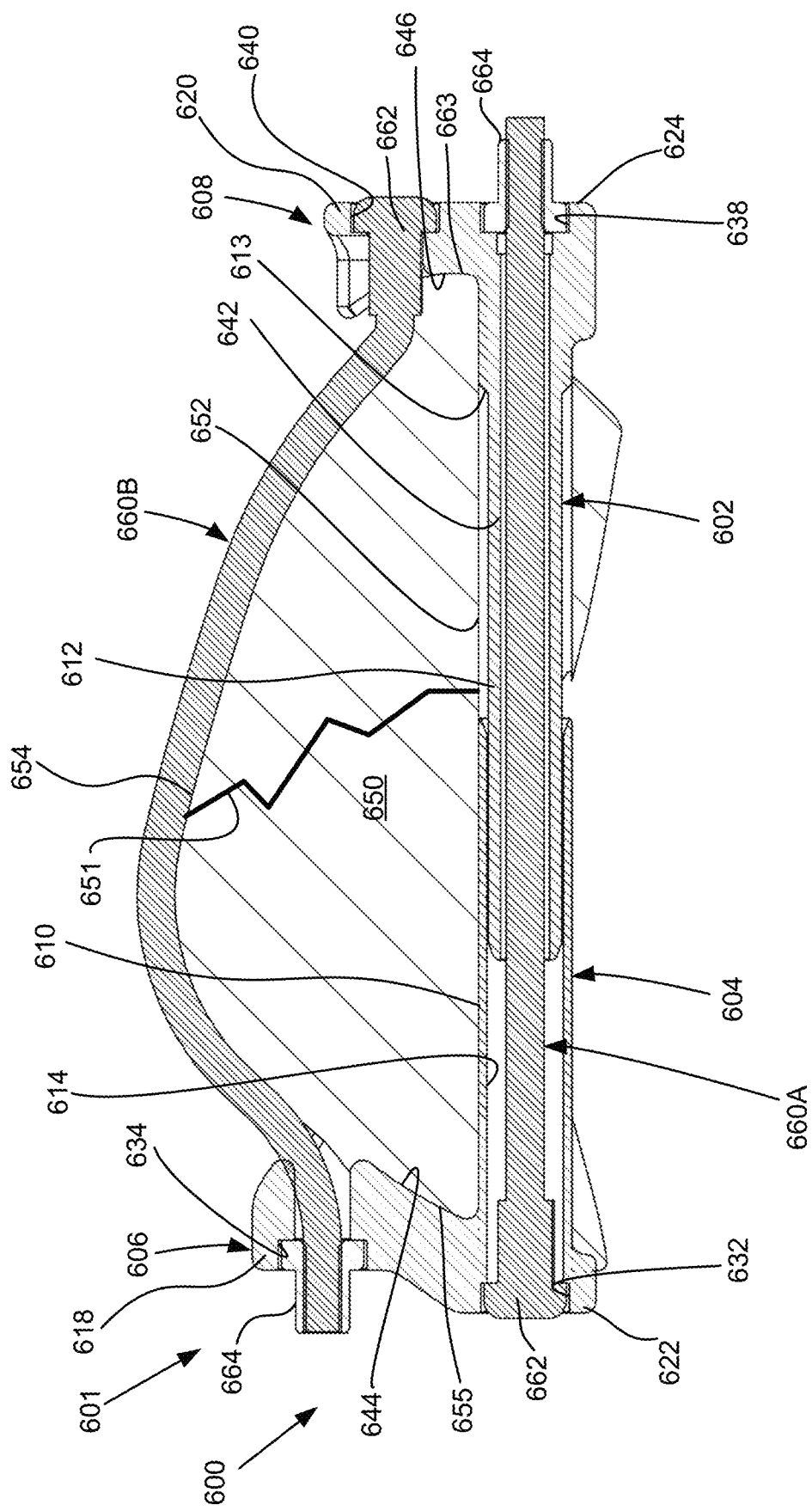
FIG. 13 is a cross-sectional side elevation view of a washer system, including the washer assembly of FIG. 7, a first cable, and a second cable, reducing and stabilizing a fracture in a bone, according to one or more embodiments of the present disclosure.

The first portion 602 of the washer assembly 600 includes a first washer 606, a first stem 610, and a first internal channel 614. The first washer 606 has features and provides advantages similar to the other washers (e.g., washer 100) described herein. For example, the first washer 606 is configured to support a cable extending from a pass-through hole in bone and/or a cable extending around the bone. The first washer 606 includes a bone-engaging surface 644 that is contoured or curved to complement a shape of a bone on which the first washer 606 is to be seated. For example, as shown in FIG. 13, the bone-engaging surface 644 is substantially concave and curved to approximately match the curvature of a surface of a bone at a particular location on the bone (e.g., the first surface 655 at a first portion of the bone 650). In the illustrated embodiment, the bone-engaging surface 644 is formed in a base 622 and a first arm 618 coupled to and extending from the base 622. The first arm 618 of the first washer 606 is formed together with the base 622 to form a one-piece monolithic construction with the base 622 in some embodiments. In some embodiments, the first washer 606 does not include a first arm 618, but rather has only a base 622. Alternatively, in other embodiments, the first washer 606 includes more than one first arm 618 coupled to and extending from the base 622 in a spaced apart manner relative to each other (see, e.g., FIG. 3).

The first stem 610 is coupled to and extends from the base 622 of the first washer 606. Similar to the arm 618, the first stem 610 of the first washer 606 is formed together with the base 622 to form a one-piece monolithic construction with the base 622 in some embodiments. The first stem 610 extends from the base 622 in a direction that is substantially orthogonal to the direction that the arm 618 extends from the base 622. Moreover, the first stem 610 is elongate in the direction from which it extends from the base 622 of the first washer 606. In the illustrated embodiment, the exterior surface of the first stem 610 has a substantially circular shape in cross-section. In other embodiments, the exterior surface of the first stem 610 has a substantially non-circular shape in cross-section.

The first portion 602 is cannulated via the first internal channel 614 defined by the first washer 606 and the first stem 610 of the first portion 602 of the washer assembly 600. More specifically, in certain implementations, the first internal channel 614 is a pass-through hole that extends entirely through the base 622 of the first washer 606 and the first stem 610. Generally, the first internal channel 614 has a first axis 615 that is coaxial with the first stem 610. In the illustrated embodiment, the first internal channel 614 has a generally circular-shaped cross-section along a plane perpendicular to the first axis 615. However, in other embodiments, as will be explained in more detail below, to prevent relative rotation of the first portion 602 and the second portion 604, the first internal channel 614 has a cross-section, along a plane perpendicular to the first axis 615, that has a non-circular shape (e.g., square, rectangular, ovular, and the like). Generally, in some implementations, the shape and cross-sectional area of the first internal channel 614 is constant along the entire length of the first internal channel 614.

In some embodiments, the first washer 606 includes a first external recess 632 that is contiguous with the first internal channel 614. More specifically, the first external recess 632 is formed into an exterior surface of the first washer 606 at a location such that the first external recess 632 is open to the first internal channel 614. In one implementation, the first external recess 632 is coaxial with the first internal channel 614. The first external recess 632 can have any of various cross-sectional shapes, however, in one implementation the first external recess 632 has a circular-shaped cross-section. Generally, the first external recess 632 has a greater major dimension (e.g., diameter) than the first internal channel 614.

The first arm 618 of the first washer 606 extends substantially orthogonally relative to or away from the first axis 615 of the first internal channel 614. The first washer 606 includes a third internal channel 616 defined by the first arm 618. The third internal channel 616 is a pass-through hole that extends entirely through the first arm 618 of the first washer 606. In one implementation, the third internal channel 616 has a central axis that is substantially parallel to and offset from the central axis 615 of the first internal channel 614. The first arm 618 further includes a first notch 626 formed in a side of the first arm 618 and open to an inward end of the third internal channel 616. The first notch 626 is sized to at least partially receive a portion of a cable 660A so as to facilitate the relatively sharp or abrupt redirection of a cable 660A, extending around a bone, as the cable 660A exits or enters the inward end of the third internal channel 616 (see, e.g., FIG. 13).

In some embodiments, the first washer 606 includes a third external recess 634 that is contiguous with the third internal channel 616 defined by the first arm 618. More specifically, the third external recess 634 is formed into an exterior surface of the first arm 618 of the first washer 606 at a location such that the third external recess 634 is open to the third internal channel 616. In one implementation, the third external recess 634 is coaxial with the third internal channel 616. The third external recess 634 can have any of various cross-sectional shapes, however, in one implementation the third external recess 634 has a circular-shaped cross-section. Generally, the third external recess 634 has a greater major dimension (e.g., diameter) than the third internal channel 616. The third external recess 634 can be co-planar with, or axially offset from (see, e.g., FIGS. 10-12), the first external recess 632.

The first washer 606 and the first stem 610 of the first portion 602 of the washer assembly 600 can be made of the same material and, as mentioned above, collectively form a one-piece monolithic construction. In one implementation, the first portion 602 is made of a metal, such as stainless steel or titanium. In another implementation, the first portion 602 is made of a polymeric material.

Similar to the first portion 602 of the washer assembly 600, the second portion 604 of the washer assembly 600 includes a second washer 608, a second stem 612, and a second internal channel 642. The second washer 608 has features and provides advantages similar to the other washers (e.g., washer 100) described herein. For example, the second washer 608 is configured to support a cable extending from a pass-through hole in bone and/or a cable extending around the bone. The second washer 608 includes a bone-engaging surface 646 that is contoured or curved to complement a shape of a bone on which the second washer 608 is to be seated. For example, as shown in FIG. 13, the bone-engaging surface 646 is substantially concave and curved to approximately match the curvature of a surface of a bone at a particular location on the bone (e.g., the second surface 655 at a second portion of the bone 650). The bone-engaging surface 646 of the first portion 602 is configured differently than the bone-engaging surface 644 of the second portion 604 to accommodate non-symmetrically shaped bones. Accordingly, the first washer 606 is configured differently than the second washer 608.

In the illustrated embodiment, the bone-engaging surface 646 is formed in a base 624 and a second arm 620 coupled to and extending from the base 624. The second arm 620 of the second washer 608 is formed together with the base 624 to form a one-piece monolithic construction with the base 624 in some embodiments. In some embodiments, the second washer 608 does not include a second arm 620, but rather has only a base 624. Alternatively, in other embodiments, the second washer 608 includes more than one second arm 620 coupled to and extending from the base 624 in a spaced apart manner relative to each other (see, e.g., FIG. 3).

The second stem 612 is coupled to and extends from the base 624 of the second washer 608. Similar to the second arm 620, the second stem 612 of the second washer 608 is formed together with the base 624 to form a one-piece monolithic construction with the base 624 in some embodiments. The second stem 612 extends from the base 622 in a direction that is substantially orthogonal to the direction that the second arm 620 extends from the base 624. Moreover, the second stem 612 is elongate in the direction from which it extends from the base 624 of the second washer 608.

According to some embodiments, the exterior surface of the second stem 612 complements or matches the interior surface of the first internal channel 614 defined by the first stem 610. More specifically, the exterior surface of the second stem 612 is configured such that the second stem 612 is insertable into the first internal channel 614 of the first stem 610, movable within the first internal channel 614, and nestably or complementary engaged with the first internal channel 614 to form a tight, telescoping, fit between the second stem 612 and the first stem 610. In the illustrated embodiment, the exterior surface of the second stem 612 is circular to match the circular cross-sectional shape of the first internal channel 614. Moreover, the diameter of the exterior surface of the second stem 612 is approximately equal to (e.g., just fractionally smaller than) that of the first internal channel 614 to reduce play or wiggle between the first stem 610 and the second stem 612 when engaged. The diameter of the first internal channel 614 is greater than the diameter of the second internal channel 642.

Because the cross-sectional shapes of the exterior surface of the second stem 612 and the first internal channel 614 are circular, in some embodiments, the first portion 602 is rotatable relative to the second portion 604. Such a configuration accommodates for differently sized and shaped bones. However, in other embodiments, the first internal channel 614 has a non-circular shape and the exterior surface of the second stem 612 has the same non-circular shape, which allows slidable movement of the second stem 612 within the first internal channel 614 but prevents rotation of the second stem 612 relative to the first internal channel 614. Such a configuration ensures the first washer 606 remains in a desired orientation relative to the second washer 608 regardless of the size or shape of a bone.

The second stem 612 may include a shoulder 613, between the second washer 608 and a distal end of the second stem 612, that is enlarged relative to the rest of the second stem 612. In other words, the shoulder 613 has an external surface with a diameter greater than that of the rest of the second stem 612. The shoulder 613 acts as a stop to prevent further movement of the first stem 610 of the first portion 602 toward the second washer 608 of the second portion 604. In this manner, the shoulder 613 helps to define a minimum distance L3 between the first washer 606 and the second washer 608 (see, e.g., FIG. 12). Additionally, the distal end of the second stem 612 may be beveled, which, when engaged with the distal end of the first stem 610, promotes proper positioning or alignment of the second stem 612 relative to the first stem 610 as the second stem 612 is being inserted into the first internal channel 614 of the first stem 610.

The second portion 604 is cannulated via the second internal channel 642 defined by the second washer 608 and the second stem 612 of the second portion 604 of the washer assembly 600. More specifically, in certain implementations, the second internal channel 642 is a pass-through hole that extends entirely through the base 624 of the second washer 608 and the second stem 612. Generally, the second internal channel 642 has a second axis 643 that is coaxial with the second stem 612 and coaxial with the first axis 615 of the first internal channel 614 when the second stem 612 is nestably engaged with the first stem 610. In the illustrated embodiment, the second internal channel 642 has a generally circular-shaped cross-section along a plane perpendicular to the second axis 643. In some implementations, the shape and cross-sectional area of the second internal channel 642 is constant along the entire length of the second internal channel 642. The size and shape of the second internal channel 642 is selected to complement the size and shape of the cable 660A passing through the washer assembly 600. In one implementation, the second internal channel 642 is sized and shaped to form a relatively tight fit between the cable 660A and the second internal channel 642, but allow the cable 660A to slide or move through the second internal channel 642. In this manner, the cable 660A can be moved through the first internal channel 614 and the second internal channel 642 with the cable 660A being retained in coaxial alignment with the first axis 615 and the second axis 643.

In some embodiments, the second washer 608 includes a second external recess 638 that is contiguous with the second internal channel 642. More specifically, the second external recess 638 is formed into an exterior surface of the second washer 608 at a location such that the second external recess 638 is open to the second internal channel 642. In one implementation, the second external recess 638 is coaxial with the second internal channel 642. The second external recess 638 can have any of various cross-sectional shapes, however, in one implementation the second external recess 638 has a circular-shaped cross-section. Generally, the second external recess 638 has a greater major dimension (e.g., diameter) than the second internal channel 642.

The second arm 620 of the second washer 608 extends substantially orthogonally relative to or away from the second axis 643 of the second internal channel 642. The second washer 608 includes a fourth internal channel 636 defined by the second arm 620. The fourth internal channel 636 is a pass-through hole that extends entirely through the second arm 620 of the second washer 608. In one implementation, the fourth internal channel 636 has a central axis that is substantially parallel to and offset from the central axis 643 of the second internal channel 642. The second arm 620 further includes a second notch 628 formed in a side of the second arm 620 and open to an inward end of the fourth internal channel 636. The second notch 628 is sized to at least partially receive a portion of a cable 660B so as to facilitate the relatively sharp or abrupt redirection of a cable 660B, extending around a bone, as the cable 660B exits or enters the inward end of the fourth internal channel 636 (see, e.g., FIG. 13).

In some embodiments, the second washer 608 includes a fourth external recess 640 that is contiguous with the fourth internal channel 636 defined by the second arm 620. More specifically, the fourth external recess 640 is formed into an exterior surface of the second arm 620 of the second washer 608 at a location such that the fourth external recess 640 is open to the fourth internal channel 636. In one implementation, the fourth external recess 640 is coaxial with the fourth internal channel 636. The fourth external recess 640 can have any of various cross-sectional shapes, however, in one implementation the fourth external recess 640 has a circular-shaped cross-section. Generally, the fourth external recess 640 has a greater major dimension (e.g., diameter) than the fourth internal channel 636. The fourth external recess 640 can be co-planar with (see, e.g., FIGS. 10-12), or axially offset from, the third external recess 638.

The second washer 608 and the second stem 612 of the second portion 604 of the washer assembly 600 can be made of the same material and, as mentioned above, collectively form a one-piece monolithic construction. In one implementation, the second portion 604 is made of a metal, such as stainless steel or titanium. In another implementation, the second portion 604 is made of a polymeric material.

When nestably engaged, the first portion 602 is movable (e.g., slidable or translationally movable) relative to the second portion 604 to adjust the distance between the first washer 606 and the second washer 608. For example, the distance between the first washer 606 and the second washer 608 can be adjusted between a maximum distance L1 (see, e.g., FIG. 10) and a minimum distance L3 (see, e.g., FIG. 12), inclusively. Additionally, the distance can be set to any of various distances between the maximum distance L1 and the minimum distance L3, such as an intermediate distance L2 (see, e.g., FIG. 11). The adjustability of the distance between first washer 606 and the second washer 608 helps to accommodate different bone sizes with a single washer assembly 600.

Referring to FIG. 13, the washer system 601 includes the washer assembly 600 and at least one cable (e.g., at least one of cables 660A, 660B). The washer assembly 600 is shown with the second stem 612 nestably engaged with the first stem 610. The first stem 610 and the second stem 612 are positioned within a pass-through hole 652 formed in the bone 650. The pass-through hole 652 extends through the bone 650 and transverses a fracture 651 in the bone 650. Accordingly, at least one of the first stem 610 and the second stem 612 also transverses the fracture 651 in the bone. With the first stem 610 and the second stem 612 positioned within the pass-through hole 652, the first washer 606 and the second washer 608 rest in compression against opposing respective exterior surfaces 655, 663 of the bone 650. At least a portion of the compression of the first washer 606 and the second washer 608 against the bone 650 is induced via the cable 660A, which is passed through the first internal channel 614 of the first stem 610 and the second internal channel 642 of the second stem 612 and placed in tension. Further fixation of the washer assembly 100 relative to the bone 650, and further compression of the first washer 606 and the second washer 608 against the bone, is accomplished by an additional cable 660B that is passed through the third internal channel 616 of the first washer 606, around the bone 650, and through the fourth internal channel 636 of the second washer 608, and placed in tension.

In the illustrated embodiment, the coupling element is the cable 660A. Moreover, each of the cables 660A, 660B includes a stop 662 at one of a first end portion or a second end portion of the cable 660. The stop 662 can be co-formed with the cable to form a one-piece monolithic unit with the cable. Alternatively, the stop 662 can be formed separately from the cable and non-movably pre-attached to the first end portion or second end portion of each of the cables 660A, 660B prior to inserting the cable 660A through the first internal channel 614 and the second internal channel 642 or prior to positioning the cable 660B about the bone 650. The stop 662 is configured to be seatably engaged with one of the first external recess 632 or the second external recess 638, or one of the third external recess 634 or fourth external recess 640. Furthermore, the stop 662 has cross-sectional shape with a major dimension (e.g., diameter) greater than a major dimension of the respective one of the cables 660A, 660B. The stop 662 of the cable 660A extending through the bone 650 can be considered a first stop and the stop 662 of the cable 660B extending around the bone 650 can be considered a second stop.

The washer system 601 further includes a crimp body 664 crimped to the other of the first end portion or the second end portion of each of the cables 660A, 660B or the end portion of each of the cables 660A, 660B opposite the stop 662. The crimp body 664 is crimped to respective cables 660A, 660B after being tensioned such that the crimp body 664 is non-movably fixed to respective cables 660A, 660B. The crimp body 664 is configured to be seatably engaged with the other one of the first external recess 632 or the second external recess 638, or the other one of the third external recess 634 or fourth external recess 640. With the cables 660A, 660B in tension, engagement between the crimp body 664 one of the external recesses and engagement between the stop 662 and the other of the external recesses, the cables 660A, 660B remains in tension. The crimp body 664 crimped to the cable 660A extending through the bone 650 can be considered a first crimp body and the crimp body 664 crimped to the cable 660B extending around the bone 650 can be considered a second crimp body.

Figure 14:
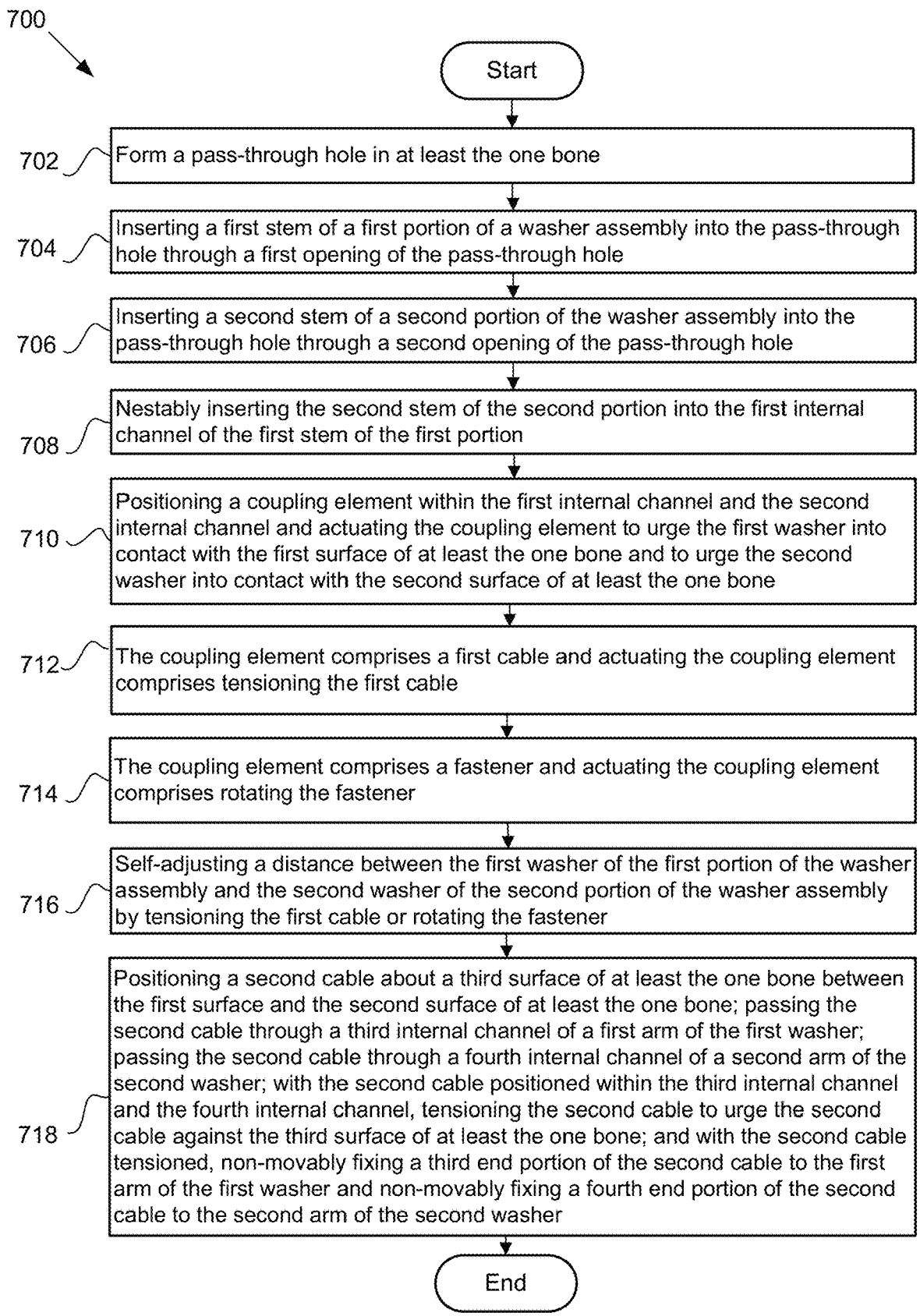
FIG. 14 is schematic flow diagram of a method of reducing and stabilizing at least one of a fracture in, a dislocation of, or a subluxation of at least one bone, according to one or more embodiments of the present disclosure.

Referring to FIG. 14, one embodiment of a method 700 of reducing and stabilizing at least one of a fracture in, a dislocation of, or a subluxation of at least one bone is shown. The method 700 may be executed using the washer system 601 and will hereafter be described accordingly. The method 700 includes forming a pass-through hole 652 in at least one bone 650 at 702. The bone 650 may have a fracture 651 through which the pass-through hole 652 extends. The pass-through hole 652 can be formed using any of various techniques, such as, but not limited to, driving a rotating drill bit through the bone 650. The method 700 further includes inserting the first stem 610 of the first portion 602 of the washer assembly 600 into the pass-through hole 652 through a first opening, on a first external surface 655 of the bone 650, of the pass-through hole 652 at 704. The method 700 also includes inserting the second stem 612 of the second portion 604 of the washer assembly 600 into the pass-through hole 652 through a second opening, on a second external surface 663 of the bone 650, of the pass-through hole 652 at 706.

With the first stem 610 and the second stem 612 inserted into the pass-through hole 652, the method 700 additionally includes nestably inserting the second stem 612 of the second portion 604 into the first internal channel 614 of the first stem 610 of the first portion 602 at 708. Accordingly, the first stem 610 and the second stem 612 of the washer assembly 600 are nestably engaged within the pass-through hole 652. The method 700 may additionally include positioning a coupling element within the first internal channel and the second internal channel and actuating the coupling element to urge the first washer into contact with the first surface of at least the one bone and to urge the second washer into contact with the second surface of at least the one bone at 710.

At 712 of the method 700, the coupling element comprises a first cable and actuating the coupling element comprises tensioning the first cable. While the first stem 610 and the second stem 612 are nestably engaged, the method 700 may include passing a first cable 660A through the first internal channel 614 of the first portion 602 and the second internal channel 642 of the second portion 604. Passing the first cable 660A through the first internal channel 614 and the second internal channel 642 necessarily includes passing the first cable 660A through the pass-through hole 652. As mentioned above, tensioning the first cable 660A urges the first washer 606 against or into contact with the first surface 655 of the bone 650 and urges the second washer 608 against or into contact with the second surface 663 of the bone 650 at 712. In other words, tensioning the first cable 660A draws the first washer 606 and the second washer 608 toward each other to reduce the distance between the first washer 606 and the second washer 608 and to effectively compressively clamp the bone 650 between the first washer 606 and the second washer 608. The first cable 660A can be tensioned using any of various tensioning devices.

With the first cable 660A tensioned, the method 700 may include non-movably fixing a first end portion of the first cable 660A to the first washer 606 and non-movably fixing a second end portion of the first cable 660B to the second washer 608. Non-movably fixing the first end portion of the first cable 660A to the first washer 606 can be accomplished via one of the stop 662 or the crimp 664 and non-movably fixing the second end portion of the first cable 660A to the second washer 608 can be accomplished via the other one of the stop 662 or the crimp 664. In one implementation, the first cable 660A is passed through the first internal channel 614 and the second internal channel 642 until the stop 662 is seated in one of the external recesses 632, 638, then the first cable 660A is tensioned, and finally the crimp 664 is seated within the other of the external recesses 632, 638 and crimped to the first cable 660A to permanently maintain the tension in the first cable 660A. In some implementations, at 714 of the method 700, the coupling element comprises a fastener and actuating the coupling element comprises rotating the fastener. At 716, the method 700 further includes self-adjusting the distance between the first washer 606 and the second washer 608 by tensioning the first cable 660A or rotating the fastener 880. Generally, tensioning the first cable 660A involves anchoring a tensioner against the washer assembly 600 such that tensioning the first cable 660A necessarily draws the first washer 606 and the second washer 608 together. Rotating the fastener 880 can include using a tightening or torqueing tool, such as a drill or screwdriver.

In some implementations, at 718, the method 700 also includes positioning a second cable 660B about a third surface 654 of at least the one bone 650 between the first surface 655 and the second surface 663 of at least the one bone 650, passing the second cable 660B through a third internal channel 616 of a first arm 618 of the first washer 606, passing the second cable 660B through a fourth internal channel 636 of a second arm 620 of the second washer 608, tensioning the second cable 660B to urge the second cable 660B against the third surface 654 of at least the one bone 650, and, with the second cable 660B tensioned, non-movably fixing a third end portion of the second cable 660B to the first arm 618 of the first washer 606 and non-movably fixing a fourth end portion of the second cable 660B to the second arm 620 of the second washer 608. Non-movably fixing the first end portion of the second cable 660B to the first arm 618 of the first washer 606 can be accomplished via one of the stop 662 or the crimp 664 and non-movably fixing the second end portion of the second cable 660B to the second arm 620 of the second washer 608 can be accomplished via the other one of the stop 662 or the crimp 664. In one implementation, the second cable 660B is passed through one of the third internal channel 616 or the fourth internal channel 636, extended around the third surface 654 of the bone 650, and passed through the other of the third internal channel 616 or the fourth internal channel 636 until the stop 662 is seated in one of the external recesses 634, 640, then the second cable 660B is tensioned, and finally the crimp 664 is seated within the other of the external recesses 634, 640 and crimped to the second cable 660B to permanently maintain the tension in the second cable 660B.

Figure 15:
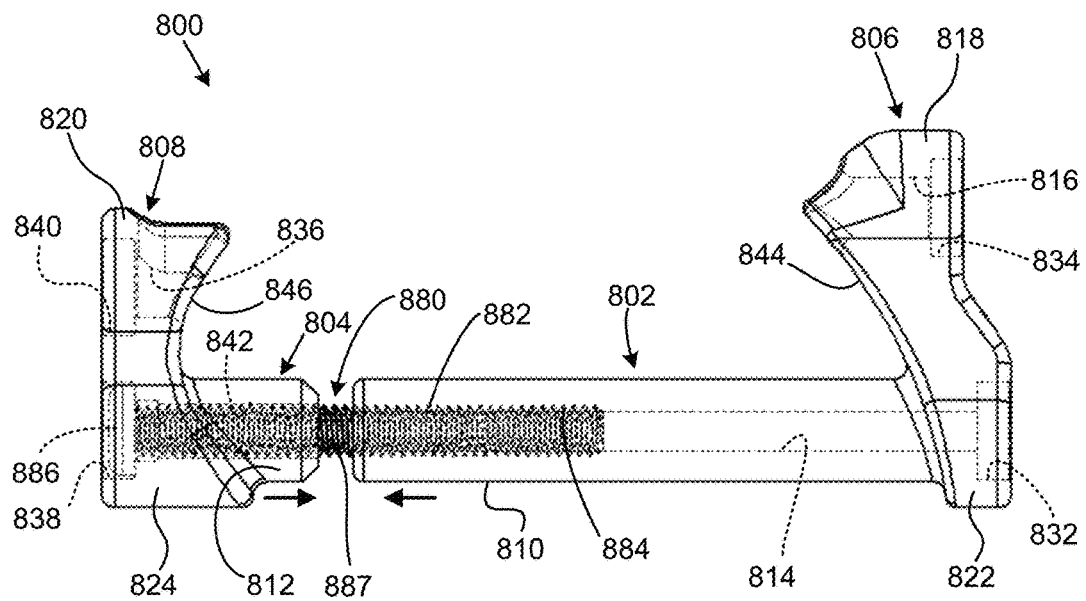
FIG. 15 is a side elevation view of another washer assembly, according to one or more embodiments of the present disclosure.
Figure 16:
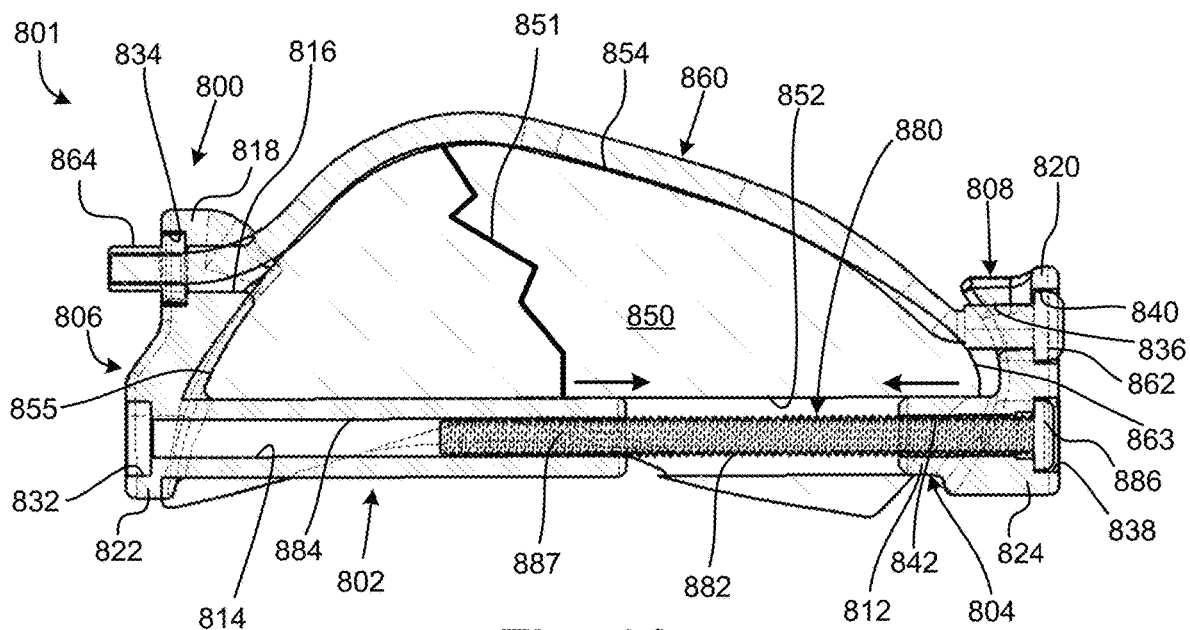
FIG. 16 is a cross-sectional side elevation view of another washer system, including the washer assembly of FIG. 15 and a second cable, reducing and stabilizing a fracture in a bone, according to one or more embodiments of the present disclosure.

FIGS. 15 and 16 show embodiments of a washer assembly 800 and a washer system 801, respectively. Generally, the washer system 801 includes the washer assembly 800 and at least one cable 860. The washer assembly 800 of FIG. 15 is analogous to the washer assembly 600 of FIGS. 7-12, with like numbers referring to like features, and the washer system 801 of FIG. 16 is analogous to the washer system 601 of FIG. 13, with like numbers referring to like features. More specifically, features of the washer assembly 600 and the washer system 601 that are analogous to features of the washer assembly 800 and the washer system 801 have the same number, but in a different series (e.g., 800-series) format rather than the 600-series format of the washer assembly 600 and the washer system 601. Therefore, unless otherwise noted, the description, including the structure, function, and advantages, of the features of the washer assembly 600 and the washer system 601 presented above are applicable to the analogous features of the respective washer assembly 800 and the washer system 801 of FIGS. 15 and 16.

Like the washer assembly 600, the washer assembly 800 includes a first stem 810, which has a first internal channel 814, and a second stem 812, which has a second internal channel 842. However, in contrast to the washer assembly 600, the second stem 812 is not insertable into and movable within the first internal channel 814 of the first stem 810. Rather, the second internal channel 842 is sized to receive (such as via nested or threaded engagement) a fastener 880, which is the coupling element of the washer assembly 800, and the first internal channel 814 is configured to receive via threaded engagement the fastener 880. The fastener 880 includes a head 886 and a shaft 887. The head 886 has a larger cross-sectional dimension (e.g., diameter) than the shaft 887. At least a portion of the shaft 887 is threaded. More specifically, at least a portion of the shaft 887 includes external threads 882 that are configured to threadably engage internal threads 884 formed in the first internal channel 814.

The washer assembly 600 is assembled by inserting the shaft 887 into and through the second internal channel 842 and threadably engaging the external threads 882 of the shaft 887 with the internal threads 884 of the first internal channel 814. Further engagement of the external threads 882 with the internal threads 884 via rotation of the fastener in a tightening direction (e.g., clockwise direction) draws the first washer 806 and the second washer 808 together as indicated by opposing directional arrows. Moreover, the shaft 887 of the fastener 880, being rigid, straight, and engaged with the second internal channel 842 and threadably engaged with the first internal channel 814, maintains the first washer 806 and the second washer 808 in alignment. In other words, the shaft 887 of the fastener 880 keeps the first internal channel 814 and the second internal channel 842 in coaxial alignment. The head 886 is configured to sit within the second external recess 638 of the second washer 808 when the washer assembly 600 is tightened against a bone, such as bone 850, as will be described in more detail below.

An overall length of the washer assembly 800 (e.g., a distance between the first washer 806 and the second washer 808) is adjustable from a minimum length, at which the first stem 802 abuts the second stem 804, to a maximum length, at which a minimum threshold of external threads 882 of the shaft 887 are engaged with internal threads 884 of the first internal channel 814. Although the first stem 810 and the second stem 812 are shown not to be nestably engageable, in some embodiments, if desired, portions of the first stem 810 and the second stem 812 can be nestably engageable even with the fastener 880 being threaded or otherwise engaged with the first internal channel 814 and the second internal channel 842.

Referring now to FIG. 16, the washer system 801 is shown engaged with and fixed relative to the bone 850. The first stem 810 and the second stem 812 are positioned within the pass-through hole 852 formed in the bone 850. With the first stem 810 and the second stem 812 positioned within the pass-through hole 852, the first washer 806 and the second washer 808 rest in compression against opposing respective exterior surfaces 855, 863 of the bone 850. However, instead of a flexible and tensionable cable, at least a portion of the compression of the first washer 806 and the second washer 808 against the bone 850 is induced via engagement between the fastener 880 and the first washer 806 and the second washer 808. Then, like the washer system 601, further fixation of the washer assembly 800 relative to the bone 850, and further compression of the first washer 806 and the second washer 808 against the bone, is accomplished by a cable 660 that is passed through the third internal channel 816 of the first washer 806, around the bone 850, and through the fourth internal channel 836 of the second washer 808, and placed in tension.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, or item C" may mean item A; item A and item B; item B; item A, item B, and item C; or item B and item C; or some other suitable combination. In some cases, "at least one of item A, item B, or item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A washer system for supporting at least one cable extending at least one of around a bone or through a pass-through hole formed in the bone, comprising:

a washer assembly, comprising:
  a first portion, comprising a first washer, a first stem non-movably fixed to and extending from the first washer, and a first internal channel passing through the first washer and the first stem; and
  a second portion, comprising a second washer, a second stem non-movably fixed to and extending from the second washer, and a second internal channel passing through the second washer and the second stem;
  wherein the first portion is movable relative to the second portion, to adjust a distance between the first washer and the second washer, and the first internal channel is retained in coaxial alignment with the second internal channel as the first portion moves relative to the second portion; and
a coupling element releasably coupled to the first portion and the second portion, reversibly decouplable from the first portion and the second portion, and positioned within the first internal channel of the first portion of the washer assembly and within the second internal channel of the second portion of the washer assembly, wherein the coupling element is actuatable to move the first portion relative to the second portion;
wherein:
  the coupling element comprises a first cable;
  with the first cable positioned within the first internal channel and the second internal channel, a first end portion of the first cable is coupled with the first washer and a second end portion of the first cable is coupled with the second washer;
  the first cable is tensionable to adjust the distance between the first washer and the second washer;
  the second stem of the second portion is nestably inserted within and translationally movable along the first internal channel of the first portion to adjust the distance between the first washer and the second washer;
  the first washer comprises a first external recess contiguous with the first internal channel;
  the second washer comprises a second external recess contiguous with the second internal channel;
  the first cable comprises a first stop at one of the first end portion or the second end portion of the first cable, the first stop being seatably engaged with one of the first external recess or the second external recess; and
  the washer system further comprising a first crimp body crimped to the other of the first end portion or the second end portion of the first cable, the first crimp body being seatably engaged with the other of the first external recess or the second external recess.

2. The washer system according to claim 1, wherein an outer diameter of the cable is approximately equal to an inner diameter of second internal channel.

3. The washer system according to claim 1, wherein:
the first washer comprises a first arm, extending radially away from the first internal channel, and a third internal channel defined by the first arm and spaced apart from the first internal channel;
the second washer comprises a second arm, extending radially away from the second internal channel, and a fourth internal channel defined by the second arm and spaced apart from the second internal channel; and
the washer system further comprises a second cable comprising a third end portion and a fourth end portion, the third end portion of the second cable being positioned within the third internal channel and coupled with the first arm of the first washer and the fourth end portion of the second cable being positioned within the fourth internal channel and coupled with the second arm of the second washer.

4. The washer system according to claim 3, wherein:
the first washer comprises a third external recess contiguous with the third internal channel;
the second washer comprises a fourth external recess contiguous with the fourth internal channel;
the second cable comprises a second stop at one of the third end portion or the fourth end portion of the second cable, the second stop being seatably engaged with one of the third external recess or the fourth external recess; and
the washer system further comprising a second crimp body crimped to the other of the third end portion or the fourth end portion of the second cable, the second crimp body being seatably engaged with the other of the third external recess or the fourth external recess.

5. The washer system according to claim 1,
wherein one of:
  the second stem of the second portion is nestably inserted within and translationally movable along the first internal channel of the first portion to adjust the distance between the first washer and the second washer; or
  the first stem of the first portion is nestably inserted within and translationally movable along the second internal channel of the second portion to adjust the distance between the first washer and the second washer.

6. The washer system according to claim 5, wherein:
the first internal channel extends entirely through the first washer and the first stem; and
the second internal channel extends entirely through the second washer and the second stem.

7. The washer system according to claim 5, wherein the first internal channel of the first washer is open to the second internal channel of the second washer as the first portion moves relative to the second portion.

8. The washer assembly according to claim 1, wherein the first washer has at least one of a different size or a different shape compared to the second washer.

9. The washer assembly according to claim 1, wherein:
the first washer of the first portion comprises a first bone-engaging surface;
the second washer of the second portion comprises a second bone-engaging surface; and
the first bone-engaging surface and the second bone-engaging surface are curved.

10. The washer assembly according to claim 9, wherein the first bone-engaging surface has a shape different than that of the second bone-engaging surface.

11. The washer assembly according to claim 1, wherein:
the first washer comprises a first external recess contiguous with the first internal channel; and
the second washer comprises a second external recess contiguous with the second internal channel.

12. The washer assembly according to claim 1, wherein an outer diameter of the second stem of the second portion is approximately equal to an inner diameter of the first internal channel of the first portion.

13. The washer assembly according to claim 1, wherein the first stem of the first portion is in telescoping engagement with the second stem of the second portion such that the second stem of the second portion is slidable along the first internal channel of the first portion, without rotation of the second stem relative to the first stem, to adjust the distance between the first washer and the second washer.

14. The washer assembly according to claim 1, wherein an inner diameter of the first internal channel of the first portion is larger than an inner diameter of the second internal channel of the second portion.

15. A washer system for supporting at least one cable extending at least one of around a bone or through a pass-through hole formed in the bone, comprising:
   a washer assembly, comprising:
      a first portion, comprising a first washer, a first stem non-movably fixed to and extending from the first washer, and a first internal channel passing through the first washer and the first stem; and
      a second portion, comprising a second washer, a second stem non-movably fixed to and extending from the second washer, and a second internal channel passing through the second washer and the second stem;
      wherein the first portion is movable relative to the second portion, to adjust a distance between the first washer and the second washer, and the first internal channel is retained in coaxial alignment with the second internal channel as the first portion moves relative to the second portion; and
   a coupling element releasably coupled to the first portion and the second portion, reversibly decouplable from the first portion and the second portion, and positioned within the first internal channel of the first portion of the washer assembly and within the second internal channel of the second portion of the washer assembly, wherein the coupling element is actuatable to move the first portion relative to the second portion;
   wherein:
      the coupling element comprises a first cable;
      with the first cable positioned within the first internal channel and the second internal channel, a first end portion of the first cable is coupled with the first washer and a second end portion of the first cable is coupled with the second washer;
      the first cable is tensionable to adjust the distance between the first washer and the second washer;
      the second stem of the second portion is nestably inserted within and translationally movable along the first internal channel of the first portion to adjust the distance between the first washer and the second washer;
      the first washer comprises a first arm, extending radially away from the first internal channel, and a third internal channel defined by the first arm and spaced apart from the first internal channel;
      the second washer comprises a second arm, extending radially away from the second internal channel, and a fourth internal channel defined by the second arm and spaced apart from the second internal channel; and
   the washer system further comprises a second cable comprising a third end portion and a fourth end portion, the third end portion of the second cable being positioned within the third internal channel and coupled with the first arm of the first washer and the fourth end portion of the second cable being positioned within the fourth internal channel and coupled with the second arm of the second washer.

16. The washer system according to claim 15, wherein an outer diameter of the cable is approximately equal to an inner diameter of second internal channel.

17. The washer system according to claim 15, wherein:
   the first washer comprises a third external recess contiguous with the third internal channel;
   the second washer comprises a fourth external recess contiguous with the fourth internal channel;
   the second cable comprises a second stop at one of the third end portion or the fourth end portion of the second cable, the second stop being seatably engaged with one of the third external recess or the fourth external recess; and
   the washer system further comprising a second crimp body crimped to the other of the third end portion or the fourth end portion of the second cable, the second crimp body being seatably engaged with the other of the third external recess or the fourth external recess.

18. The washer system according to claim 15, wherein one of:
   the second stem of the second portion is nestably inserted within and translationally movable along the first internal channel of the first portion to adjust the distance between the first washer and the second washer; or
   the first stem of the first portion is nestably inserted within and translationally movable along the second internal channel of the second portion to adjust the distance between the first washer and the second washer.

19. The washer system according to claim 15, wherein:
   the first internal channel extends entirely through the first washer and the first stem; and
   the second internal channel extends entirely through the second washer and the second stem.

20. The washer system according to claim 15, wherein the first internal channel of the first washer is open to the second internal channel of the second washer as the first portion moves relative to the second portion.

* * * * *